United States Patent [19]

Okazaki et al.

[11] Patent Number: 5,733,918

[45] Date of Patent: Mar. 31, 1998

[54] CONDENSED-INDAN DERIVATIVES AND PHARMACEUTICALLY ACCEPTABLE SALTS THEREOF

[75] Inventors: Shinji Okazaki, Tokyo; Tetsuji Asao, Tokorozawa; Motoji Wakida, Hidaka; Keisuke Ishida; Masato Washinosu, both of Hanno; Teruhiro Utsugi, Tokyo; Yuji Yamada, Tokorozawa, all of Japan

[73] Assignee: Taiho Pharmaceutical Co., Ltd., Tokyo, Japan

[21] Appl. No.: 578,542

[22] PCT Filed: May 18, 1995

[86] PCT No.: PCT/JP95/00944

§ 371 Date: Jan. 19, 1996

§ 102(e) Date: Jan. 19, 1996

[87] PCT Pub. No.: WO95/32187

PCT Pub. Date: Nov. 30, 1995

[30] Foreign Application Priority Data

May 20, 1994 [JP] Japan ................... 6-107190

[51] Int. Cl.⁶ .................... A61K 31/47; C07D 221/18; C07D 491/56
[52] U.S. Cl. .................... 514/284; 546/61
[58] Field of Search .................... 546/61; 514/284

[56] References Cited

FOREIGN PATENT DOCUMENTS

WO-92/21661 10/1992 European Pat. Off. .

OTHER PUBLICATIONS

Heterocyclic Chem., vol. 28, No. 7, pp. 1809–1812.
Med. Chem. Res., 3, pp. 44–51 (1993).
Anzini. ". . . quinoline derivatives with high affinity . . . for 5-HT3 serotonin sites." Chem Abs 119:173996 1993.
Dhawan. "Orinetation preferences in the sythesis of some indeno[2,1 c]quinolin-7(H) ones." Chem Abs 119:117077 1993.
Quraishi. Synthesis and biol. act. of some new 6-thiophene-7H–indeno[2,1-c]quinolines. Chem Abs 113:58890 1989.
Anzini. ". . . quinoline derivatives as potential 5–HT receptor ligands." J. Heterocyclic Chem, (28), 1809, 1991.
Chemical Abstracts, vol. 119, No. 17, Oct. 25, 1993; Abstract No. 173996h.

*Primary Examiner*—Mukund J. Shah
*Assistant Examiner*—Bruck Kifle
*Attorney, Agent, or Firm*—Nikaido Marmelstein Murray & Oram LLP

[57] ABSTRACT

A condensed-indan derivative represented by formula (1) and a pharmaceutically acceptable salt thereof:

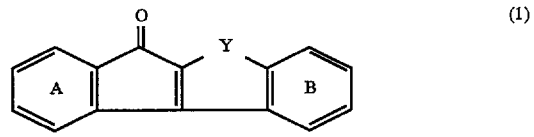

(1)

wherein ring A represents an optionally substituted benzene ring or naphthalene ring, or a benzene ring having a lower alkylenedioxy group, ring B represents an optionally substituted benzene ring or a benzene ring having a lower alkylenedioxy group. Y represents —N=CR— or —CR=N—, R represents a —NR$_1$R$_2$ group, an optionally substituted nitrogen-containing heterocyclic group or a —OR$_3$ group, wherein R$_1$ and R$_2$ are the same or different and each is a hydrogen atom; a phenyl group; an optionally substituted nitrogen-containing heterocyclic group; or a lower alkyl group which may be substituted by at least one selected from the group consisting of an optionally substituted amino group, a lower alkoxy group, a phenyl group, a nitrogen-containing heterocyclic group, an amine oxide group substituted by a lower alkyl group or a hydroxyl group(s); R$_3$ represents a lower alkyl group optionally substituted by a substituted amino group, except when R represents an optionally substituted nitrogen-containing heterocyclic group; ring A and ring B are a benzene ring having no substituent group.

16 Claims, No Drawings

CONDENSED-INDAN DERIVATIVES AND PHARMACEUTICALLY ACCEPTABLE SALTS THEREOF

TECHNICAL FIELD

The present invention relates to novel condensed-indan derivatives, pharmaceutically acceptable salts thereof, a method for producing the derivatives, composition and antitumor agent containing the derivatives and a method for treating tumor of mammal. The compounds of the invention have excellent antitumor activities, thereby useful as antitumor agent.

BACKGROUND ART

As indeno[2,1-c]quinoline derivatives, for example, compounds substituted at 6-position by a piperazinyl group described in Med. Chem. Res., 3, 44–51 (1993) are known. Although the document discloses antiserotonin activities thereof, antitumor activities of the compounds are in no way reported and described in the document. The antitumor activities of the condensed-indan derivatives of the invention are, hence, unknown.

It is an object of the invention to provide compounds which have excellent antitumor activities and are useful as medicament for treatment of tumor.

DISCLOSURE OF THE INVENTION

The present inventors have conducted research and found that condensed-indan derivatives demonstrate excellent antitumor activities and are useful as antitumor agent. Thus, the present invention has been accomplished.

The present invention provides condensed-indan derivatives represented by the formula (1) or pharmaceutically acceptable salts thereof:

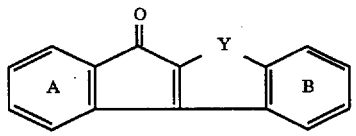

(1)

wherein ring A represents an optionally substituted benzene ring or naphthalene ring, or a benzene ring having a lower alkylenedioxy group, ring B represents an optionally substituted benzene ring or a benzene ring having a lower alkylenedioxy group. Y represents —N=CR— or —CR=N—, R represents a —NR$_1$R$_2$ group, an optionally substituted nitrogen-containing heterocyclic group or a —OR$_3$ group, wherein R$_1$ and R$_2$ are the same or different and each is a hydrogen atom; a phenyl group; an optionally substituted nitrogen-containing heterocyclic group; a lower alkyl group which may be substituted by at least one selected from the group consisting of an optionally substituted amino group, a lower alkoxy group, a phenyl group, a nitrogen-containing heterocyclic group, an amine oxide group substituted by a lower alkyl group or a hydroxyl group; R$_3$ represents a lower alkyl group optionally substituted by a substituted amino group, provided that ring A and ring B are not a benzene ring having no substituent when R represents an optionally substituted nitrogen-containing heterocyclic group.

The compounds of the present invention represented by said formula (1) has excellent antitumor activities, and are effective for treatment of a variety of tumors.

Accordingly, the invention provides a composition comprising an effective amount of the compound of said formula (1) or a pharmaceutically acceptable salt thereof and a pharmaceutically acceptable carrier therefor.

The present invention, in particular, provides an antitumor agent comprising an effective amount of the compound of said formula (1) or a pharmaceutically acceptable salt thereof and a pharmaceutically acceptable carrier therefor.

The present invention further provides a method for treating tumor of mammal which comprises administering an effective amount of the compound of said formula (1) or a pharmaceutically acceptable salt thereof to mammal.

In said formula (1), examples of groups as defined in R$_1$, R$_2$ and R$_3$ and the other groups described in the specification are shown below.

Examples of substituent groups included in benzene ring and naphthalene ring represented by ring A and ring B are halogen atom, lower alkyl group, lower alkoxy group, hydroxyl group, nitro group, amino group, lower acyloxy group, benzyloxy group, lower acylamino group, cyano group, carboxyl group, lower alkoxycarbonyl group, preferably halogen atom, lower alkyl group, lower alkoxy group, hydroxyl group, nitro group, amino group, lower acyloxy group, benzyloxy group and lower acylamino group.

Said substituent groups may be placed at any position of each ring which may have the same or different 1–4 substituent groups. With respect to ring A, preferable positions are 8-, 9- and 10-position of indeno[2,1-c]quinoline ring and indeno[2,1-c]isoquinoline ring. With respect to ring B, preferable positions are similarly 2-, 3- and 4-position. The number of substituent group in each ring are preferably 1 and 2, respectively.

Structure and substitution position of indeno[2,1-c]quinoline are shown in table 1 below, and structure and substitution position of indeno[2,1-c]isoquinoline are shown in table 5 below.

Examples of lower alkylenedioxy group are methylenedioxy, ethylenedioxy, trimethylenedioxy, tetramethylenedioxy group and like alkylenedioxy group having 1–4 carbon atoms. The substitution positions of lower alkylenedioxy group are preferably 8,9-position or 9,10-position of indeno[2,1-c]quinoline ring and indeno[2,1-c]isoquinoline ring in the case of ring A; and similarly 2,3-position or 3,4-position in the case of ring B. When ring A is an optionally substituted naphthalene ring, substitution positions of the other benzene ring which is a part of naphthalene ring combined with benzene ring in indenone skeleton are any of three cases, i.e., 8–9 position, 9–10 position and 10–11 position of ring A.

Example of halogen atoms are fluorine atom, chlorine atom, bromine atom and iodine atom.

Example of lower alkyl group are straight or branched alkyl groups having 1 to 6 carbon atoms, such as methyl, ethyl, n-propyl, isopropyl, n-butyl, isobutyl, sec-butyl, tert-butyl, pentyl, hexyl, etc.

Example of lower alkoxy group are straight or branched alkoxy groups having 1 to 6 carbon atoms, such as methoxy, ethoxy, n-propoxy, isopropoxy, n-butoxy, isobutoxy, sec-butoxy, tert-butoxy, pentyloxy, hexyloxy, etc.

Example of lower acyloxy groups are straight or branched acyloxy groups having 1 to 6 carbon atoms, such as formyloxy, acetoxy, propionyloxy, butyryloxy, 2-methylpropionyloxy, pivaloyloxy, pentanoyloxy, 3-methylbutyryloxy, hexanoyloxy, etc.

Example of lower acylamino groups are straight or branched acylamino groups having 1 to 6 carbon atoms, such as formylamino, acetylamino, propionylamino, butyrylamino, 2-methylpropionylamino, pivaloylamino, pentanoylamino, 3-methylbutyrylamino, hexanoylamino, etc.

Examples of the lower alkoxycarbonyl group are straight or branched alkoxycarbonyl groups having 2 to 7 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl, hexyloxycarbonyl, etc.

Examples of substituent groups included in nitrogen-containing heterocycles represented by R, $R_1$ and $R_2$ are lower alkyl groups, lower alkyl groups having hydroxyl group(s), preferably lower alkyl groups.

Examples of substituent groups of substituted amino groups referred to as "optionally substituted amino group" represented by $R_1$ and $R_2$ and referred to as "lower alkyl group optionally substituted by a substituted amino group" represented by $R_3$, are lower alkyl group, lower cycloalkyl group, di-loweralkylamino-alkyl group, hydroxyloweralkyl group, benzyloxycarbonyl group, lower acyl group, preferably lower alkyl group, di-loweralkylamino-alkyl group, hydroxyloweralkyl group and benzyloxycarbonyl group. Said substituted amino groups may be mono-substituted or di-substituted, preferably di-substituted.

Examples of lower alkyl group having substituted amino group are methylaminomethyl, ethylaminomethyl, methylaminoethyl, ethylaminoethyl, dimethylaminomethyl, dimethylaminoethyl, dimethylaminopropyl, diethylaminomethyl, diethylaminoethyl, diethylaminopropyl, diethylaminobutyl, diethylaminopenta-2-yl, dipropylaminoethyl, dibutylaminoethyl, dibutylaminohexyl and like mono- or di-alkylamino-alkyl groups having 1 or 2 $C_1-C_6$ alkyl moieties; N-dimethylaminoethyl-N-methylaminoethyl group, acetylaminoethyl, acetylaminopropyl, propionylaminoethyl, propionylaminopropyl, pivaloylaminoethyl, pivaloylaminopropyl and like alkyl group substituted by $C_2-C_6$ acylamino group; cyclopropylaminomethyl, cyclopentylaminomethyl, cyclopentylaminoethyl, cyclohexylaminomethyl, cyclohexylaminoethyl and like alkyl group substituted by $C_3-C_6$ cycloalkylamino group; hydroxymethylaminomethyl, 2-hydroxyethylaminomethyl, 3-hydroxypropylaminomethyl, hydroxymethylaminoethyl, 2-hydroxyethylaminoethyl, 3-hydroxypropylaminoethyl, 4-hydroxybutylaminoethyl group and like alkyl group substituted by $C_1-C_4$ hydroxyalkylamino group; benzyloxycarbonylaminomethyl, benzyloxycarbonylaminoethyl, N-benzyloxycarbonyl-N-methylaminoethyl group and like alkyl group substituted by benzyloxycarbonylamino group.

Examples of lower alkyl group having lower alkoxy group are methoxymethyl, ethoxymethyl, propoxymethyl, methoxyethyl, ethoxyethyl, methoxypropyl group and like straight or branched $C_1-C_6$ alkyl group substituted by $C_1-C_6$ alkoxy group.

Examples of lower alkyl group substituted by a phenyl group are benzyl, phenethyl, 2-phenethyl, phenylpropyl, benzhydryl, trityl group and like straight or branched $C_1-C_4$ alkyl group substituted by 1-3 phenyl groups.

Examples of nitrogen-containing heterocyclic group represented by R, $R_1$ and $R_2$ are preferably 5- or 6-membered monocyclic-type heterocyclic group having 1-4 nitrogen atoms and 0 or 1 oxygen atom or sulfur atom, specifically pyrrolyl, oxazolyl, thiazolyl, isoxazolyl, isothiazolyl, pyrazolyl, imidazolyl, oxadiazolyl, thiadiazolyl, triazolyl, oxatriazolyl, thiatriazolyl, tetrazolyl, pyridyl, pyridazinyl, pyrimidinyl, pyrazinyl, pyrrolidinyl, pyrrolinyl, imidazolidinyl, imidazolinyl, pyrazolidinyl, pyrazolinyl, piperidyl, piperidino, piperazinyl, morpholinyl, morpholino group, etc., more preferably 5- or 6-membered monocyclic-type heterocyclic group having 1-3 nitrogen atoms and 0 or 1 oxygen atom, in particular, pyridyl, pyrrolidinyl, piperidyl, piperidino, piperazinyl, morpholinyl, morpholino, 1,2,4-triazolyl group.

Examples of substituted nitrogen-containing heterocyclic group are 4-methylpiperazinyl, 4-ethylpiperazinyl, 4-methylpiperidino, 4-ethylpiperidino, 2-hydroxymethylpyrrolidinyl, 2-(2-hydroxyethyl) pyrrolidinyl, etc.

Examples of lower alkyl group having nitrogen-containing heterocyclic group represented by $R_1$ and $R_2$ are 2-pyridylmethyl, 3-pyridylmethyl, 4-pyridylmethyl, 2-pyridylethyl, 3-pyridylethyl, 4-pyridylethyl, pyrrolidinylmethyl, pyrrolidinylethyl, piperidinomethyl, piperidinoethyl, piperazinylmethyl, piperazinylethyl, morpholinomethyl, morpholinoethyl and like straight or branched $C_1-C_6$ alkyl group having nitrogen-containing heterocyclic group.

Examples of amine oxide group substituted by lower alkyl group are methylamino oxide, ethylamino oxide, butylamino oxide, dimethylamino oxide, diethylamino oxide, dibutylamino oxide and like mono- or di-alkylamino oxide group in which alkyl moieties have 1–4 carbon atoms.

Examples of lower alkyl group having an amine oxide group substituted by lower alkyl group are methylamino oxide methyl, methylamino oxide ethyl, ethylamino oxide methyl, ethylamino oxide ethyl, dimethylamino oxide methyl, dimethylamino oxide ethyl, diethylamino oxide methyl, diethylamino oxide ethyl, dibutylamino oxide propyl and like straight or branched $C_1-C_4$ alkyl group having mono- or di-alkylamino oxide group in which alkyl moieties have 1–4 carbon atoms.

Examples of lower alkyl group having hydroxyl groups are hydroxymethyl, 1-hydroxyethyl, 2-hydroxyethyl, 2-hydroxypropyl, 3-hydroxypropyl, 2,3-dihydroxypropyl, 4-hydroxybutyl, 2,3-dihydroxybutyl, 5-hydroxypentyl, 2,3-dihydroxypentyl, 6-hydroxyhexyl, 2,3-dihydroxyhexyl group and like straight or branched $C_1-C_6$ alkyl group having 1 or 2 hydroxyl groups.

Examples of the salts of the compounds of the invention are not specifically limited to, as long as the salts are pharmaceutically acceptable salts, which include salts formed with organic acids, such as formic acid, acetic acid, propionic acid, trifluoroacetic acid, tartric acid, malic acid, maleic acid, fumaric acid, succinic acid, oxalic acid, methansulfonic acid, p-toluenesulfonic acid; and inorganic acids such as hydrochloric acid, hydrobromic acid, sulfuric acid, phosphoric acid.

With respect to the compound represented by formula (1):

ring A preferably represents a benzene ring optionally substituted by hydroxyl group(s) or halogen atom(s), or a benzene ring having a lower alkylenedioxy group, more preferably represents a benzene ring optionally substituted by 1 or 2 hydroxyl groups and/or halogen atoms, or a benzene ring having a lower alkylenedioxy group;

ring B preferably represents a benzene ring substituted by hydroxyl group(s), more preferably represents a benzene ring substituted by 1 or 2 hydroxyl groups;

Y preferably represents —CR=N—;

R preferably represents a —$NR_1R_2$ group, piperazinyl group substituted by lower alkyl group, or —$OR_3$ group, more preferably represents a —$NR_1R_2$ group.

$R_1$ and $R_2$ are the same or different and each is preferably a hydrogen atom, a phenyl group or a lower alkyl group optionally substituted by an optionally substituted amino group, a nitrogen-containing heterocyclic group, an amine oxide group substituted by lower alkyl group or a hydroxy group, more preferably a hydrogen atom or a lower alkyl group optionally substituted by a diloweralkyl-substituted amino group or a nitrogen-containing heterocyclic group, in particular, $R_1$ is a lower alkyl group substituted by dimethylamino group, diethylamino group or pyrrolidinyl group and $R_2$ is a hydrogen atom; and $R_3$ preferably represents a lower alkyl group optionally substituted by diloweralkyl-substituted amino group.

The preferred compounds of the invention are indeno[2,1-c]quinoline derivatives represented by the formula (1), wherein ring A represents benzene ring unsubstituted or substituted by 1 or 2 hydroxyl group(s) and/or halogen atom(s); or a benzene ring having a lower alkylenedioxy group; ring B represents a benzene ring substituted by 1 or 2 hydroxyl group(s); Y represents —CR=N—, R represents a —$NR_1R_2$ group (wherein $R_1$ and $R_2$ are the same or different and each is a hydrogen atom or a lower alkyl group optionally substituted by a diloweralkyl-substituted amino group or a nitrogen-containing heterocyclic group), piperazinyl group substituted by lower alkyl group, or —$OR_3$ group (wherein $R_3$ represents a lower alkyl group optionally substituted by di-loweralkyl-substituted amino group).

The more preferred compounds of the invention are indeno[2,1-c]quinoline derivatives represented by the formula (1), wherein ring A represents a benzene ring unsubstituted or substituted by 1 or 2 hydroxyl groups and/or halogen atoms, or a benzene ring having a lower alkylenedioxy group; ring B represents a benzene ring substituted by 1 or 2 hydroxyl groups; Y represents —CR=N—, R represents a —$NR_1R_2$ group (wherein $R_1$ represents a lower alkyl group substituted by a diloweralkyl-substituted amino group or a nitrogen-containing heterocyclic group, in particular, lower alkyl group substituted by dimethylamino, diethylamino or pyrrolidinyl group, $R_2$ is a hydrogen atom.).

The compounds of the present invention represented by formula (1) may be produced according to the reaction formula 1 below.

<Reaction formula 1>

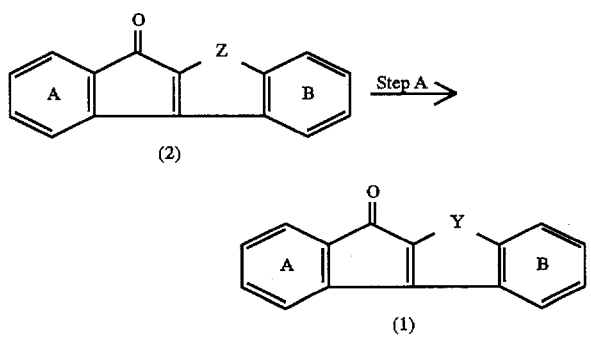

wherein ring A, ring B and Y are as defined above. Z represents —CX=N— or —N=CX—, X represents halogen atom.

(Step A)

The desired compound of the invention represented by formula (1) is produced by reacting 6-halogeno-indeno[2,1-c]quinoline derivative or 5-halogeno-indeno[2,1-c]isoquinoline derivative represented by formula (2) with amine represented by RH (which corresponds to NH($R_1$)($R_2$) or optionally substituted nitrogen-containing heterocyclic group) or alcohol ($R_3$OH) in the presence or absence of suitable solvent for amination or alkoxylation. In carrying out the amination reaction, sodium hydride, potassium tert-butoxide, sodium hydroxide, potassium hydroxide, potassium carbonate, sodium carbonate, sodium bicarbonate, triethylamine, etc., may be employed in a suitable solvent. In carrying out the alkoxylation reaction, alcohol may be employed in the form of free alcohol or alcoholate prepared by adding sodium, sodium hydride, potassium tert-butoxide, etc., to a suitable solvent.

Examples of solvent are methanol, ethanol, propanol, tert-butanol and like alcohols, dimethylformamide, dimethylacetoamide, pyridine, toluene, benzene, acetonitrile, tetrahydrofuran, water, etc. The solvents are employed singly or in a mixture of two or more of them.

In carrying out the reaction, the amine or alcohol is employed about 0.1–100 times, preferably 1–10 times as much as the molar amount of compound of formula (2). The reaction temperature is within the range of 0°–200° C., preferably 50°–150° C., and the reaction time is within the range of 0.1–100 hours, preferably 1–60 hours. These conditions are favorable to the progress of the reaction.

When ring A or ring B of compound of formula (1) obtained according to reaction formula 1 has lower alkoxy groups or benzyloxy groups as substituent groups, the substituent groups may be converted into hydroxyl group by reacting the compound with hydrobromic acid, hydroiodic acid, hydrochloric acid, sulfuric acid etc., in the presence or absence of a suitable solvent. Examples of the solvent are acetic acid and water, which may be employed singly or in a mixture of two or more of them. In carrying out the reaction, hydrobromic acid, hydroiodic acid, hydrochloric acid or sulfuric acid is employed in an amount of 0.1–1000 times (v/w), preferably 5–100 times (v/w) as much as the amount of lower alkoxy groups or benzyloxy groups. The reaction temperature is within the range of 0°–200° C., preferably 50°–150° C., and the reaction time is within the range of 0.1–100 hours, preferably 0.5–60 hours. These conditions are favorable to the progress of the reaction.

When ring A or ring B of compound of formula (1) obtained according to reaction formula 1 has a nitro group as substituent group, the nitro group may be converted into amino group by reduction, if desired. The reduction reaction may be carried out in a suitable solvent by using tin chloride in the presence of hydrochloride. Examples of the solvent are methanol, ethanol and like alcohols, dimethylformamide, etc. In carrying out the reaction, the molar amount of hydrochloride employed is preferably 1–100 times as much as the molar amount of nitro group, and the molar amount of tin chloride employed is preferably 1–10 times as much as the molar amount of nitro group. The reaction temperature is within the range of 0°–50° C., and the reaction time is within the range of 0.1–100 hours, preferably 1–12 hours. These conditions are favorable to the progress of the reaction.

When ring A or ring B of compound of formula (1) obtained according to reaction formula 1 has hydroxyl group as substituent groups, the hydroxyl group may be converted into alkoxy group, benzyloxy group or acyloxy group by alkylation, benzylation or acylation, respectively, if desired. Alkylation and benzylation reaction may be carried out in a suitable solvent by reacting alkylating agent or benzylating agent therewith in the presence of base. Examples of the solvent are dimethoxyethane, dioxane, tetrahydrofuran, dimethylformamide, acetone, etc. Examples of base are potassium carbonate, sodium carbonate, potassium hydroxide, etc. Examples of alkylating agent are halide, sulfate ester and sulfonate ester of optionally substituted alkanes. Examples of benzylating agent are benzyl halides, etc. In carrying out the reaction, the molar amount of base employed is preferably 1–5 times, the molar amount of alkylating agent or benzylating agent employed is preferably 1–5 times, as much as the molar amount of hydroxyl groups. The reaction temperature is within the range of 0°–80° C., and the reaction time is within the range of 0.1–24 hours, preferably 0.5–10 hours. These conditions are favorable to the progress of the reaction.

When R of compound of formula (1) obtained according to reaction formula 1 has an amino group substituted by a lower alkyl group, the amino group substituted by a lower alkyl group may be converted into an amineoxide group substituted by a lower alkyl group by reacting the amino group with an oxidizing agent in a suitable solvent. The solvent is not specifically limited to, as long as the solvent does not exert an adverse effect on the reaction. Examples of the solvent are ether, tetrahydrofuran and like ethers, methylene chloride, chloroform and like halogenated hydrocarbons, acetone, methylethylketone and like alkylketones, methanol, ethanol and like alcohols, N,N-dimethylformamide, dimethylsulfoxide, acetonitrile and like aprotic polar solvents, acetic acid, water, etc., which may be employed singly or in a mixture of two or more of them. Oxidizing agents are not specifically limited to, but include manganese dioxide, sodium hypochlorite, CAN(ammonium cerium (IV) nitrate), DDQ(2,3-dichloro-5,6-dicyano-1,4-benzoquinone), chloranil(2,3,5,6-tetrachloro-1,4-benzoquinone), DMSO-pyridine sulfur trioxide complex, Jones reagent, pyridinium chlorochromate, pyridinium dichromate, dimethylsulfoxide-oxalyl chloride, hydrogen peroxide, tert-butylhydroperoxide and like peroxides, performic acid, peracetic acid, m-chloroperbenzoic acid and like peracids, which may be employed singly or in a mixture thereof.

In carrying out the reaction, an oxidizing agent is employed within about 1–100 equivalent amount, preferably about 1–10 equivalent amount of the compound represented by formula (1). The reaction temperature ranges from ice-cooling to about boiling point of the solvent, and reaction time ranges from about 0.1–96 hours, preferably about 0.1 to 1 hour. These conditions are favorable to the progress of the reaction.

Acylation reaction is carried out by reacting the compound with a desired carboxylic acid or reactive derivatives thereof. When employing the reactive derivatives, the reaction is conducted in a suitable solvent optionally in the presence of base to accelerate the reaction, although the reaction conditions are varied according to kinds of the reactive derivatives and of starting phenolic derivatives. Examples of the reactive derivatives are acid anhydride, mixed acid anhydride, acid halide, etc. Examples of solvent are chloroform, dichloromethane, dioxane, tetrahydrofuran, dimethylformamide, pyridine, etc. Examples of base are sodium bicarbonate, potassium bicarbonate, triethylamine, pyridine, 4-dimethylaminopyridine, etc. In carrying out the reaction, the molar amount employed is preferably 1–5 times in base, 1–5 times in acylating agent as much as the molar amount of hydroxyl group. The reaction temperature is within the range of 0°–50° C., and the reaction time is within the range of 0.1–24 hours, preferably 0.5–3 hours. These conditions are favorable to the progress of the reaction.

When ring A or ring B of compound of formula (1) obtained according to reaction formula 1 has an amino group as substituent group, the amino group may be converted into acylamino group by acylation, if desired. The acylation reaction is carried out by reacting a desired carboxylic acid or reactive derivatives therewith. When reactive derivatives are employed, the reaction is conducted in a suitable solvent optionally in the presence of base to accelerate the reaction, although the reaction conditions are varied according to kinds of the reactive derivatives and of starting aniline derivatives. Examples of the reactive derivatives are acid anhydride, mixed acid anhydride, acid halide, etc. Examples of solvent are chloroform, dichloromethane, dioxane, tetrahydrofuran, dimethylformamide, pyridine, etc. Examples of base are sodium bicarbonate, sodium carbonate, potassium carbonate, triethylamine, pyridine, 4-dimethylaminopyridine, etc. In carrying out the reaction, the molar amount employed is preferably 1–5 times in base, 1–5 times in acylating agent as much as the molar amount of amino group. The reaction temperature is within the range of 0°–50° C., and the reaction time is within the range of 0.1–100 hours, preferably 0.5–10 hours. These conditions are favorable to the progress of the reaction.

Nitro groups may be introduced to the compound of formula (1) obtained according the reaction formula 1 by nitration reaction. The nitration reaction is conducted by using nitrating agent such as fuming nitric acid and nitric acid in the presence or absence of sulfuric acid. In carrying out the reaction, the molar amount of nitrating agent employed is preferably 1–100 times as much as the molar amount of compound of formula (1). The reaction temperature is within the range of 0°–30° C., and the reaction time is within the range of 0.1–20 hours, preferably 0.5–5 hours. These conditions are favorable to the progress of the reaction.

When R of compound of formula (1) obtained according to reaction formula 1 has protective groups, such as benzyloxycarbonyl group, lower acyl group, etc., the protective groups may be removed by reacting the protective group with hydrobromic acid, hydroiodic acid, hydrochloric acid, sulfuric acid, etc., in a suitable solvent or without solvent. The solvent includes acetic acid, water, etc., which are employed singly or in a mixture of two or more of them.

In carrying out the reaction, hydrobromic acid, hydroiodic acid, hydrochloric acid, sulfuric acid, etc., are employed in an amount ranging 1–1,000 times (v/w), preferably 5–100 (v/w) times as much as the amount of protective group. The reaction temperature is within the range of about 0°–200° C., preferably about 50°–150° C., and the reaction time is within the range of 0.1–100 hours, preferably 0.5–60 hours. These conditions are favorable to the progress of the reaction.

The compounds of the invention obtained by said reactions may be converted into salts thereof according to a conventional method by reacting the compounds with said organic acids or inorganic acids in a suitable solvent. Examples of solvent are water, methanol, ethanol, dichloromethane, tetrahydrofuran, etc. The reaction temperature is preferably within the range of 0°–50° C.

The 6-halogenoindeno[2,1-c]quinoline derivatives represented by formula (2) employed as a starting material in reaction formula 1 may be produced according to the method described in J. Heterocyclic Chem., 28, 1809 (1991), or e 2 and 3 below.

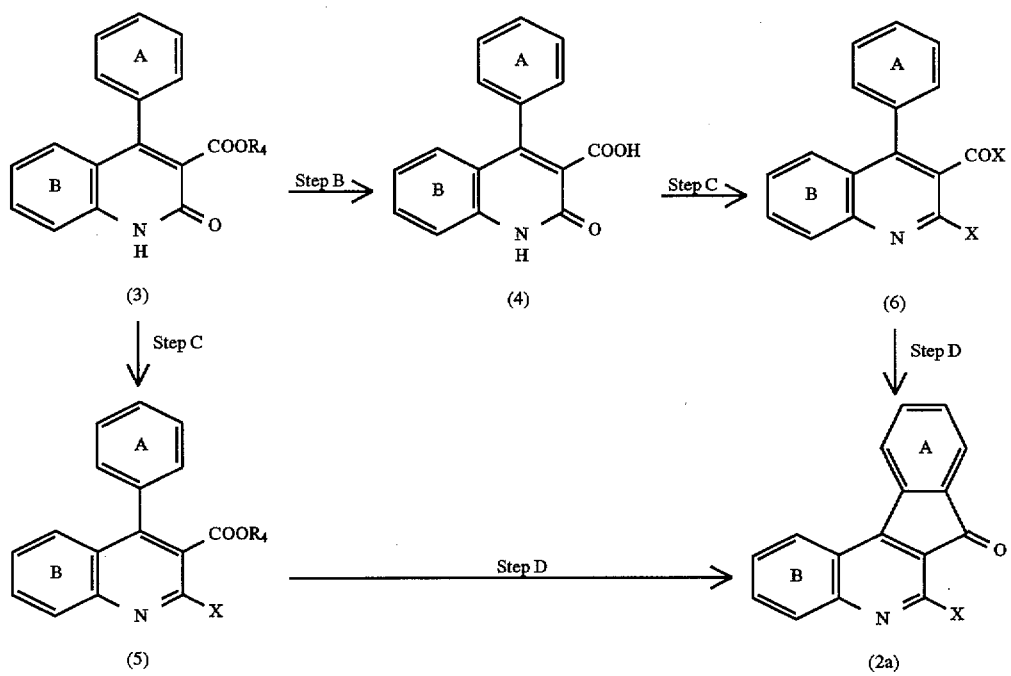

<Reaction formula 2> wherein ring A, ring B and X are as defined above. $R_4$ represents a lower alkyl group.

<Step B>

The carboxylic acid of formula (4) may be produced by hydrolyzing the compound of formula (3) in a suitable solvent with basic compound.

The compound of formula (3) may be produced according to the method disclosed in Japanese Unexamined Patent Publication No. 3-223254.

Examples of solvent are not specifically limited to, as long as the solvent does not exert an adverse effect on the reaction, but include methanol, ethanol, propanol and like alcohols, dioxane, tetrahydrofuran, dimethoxyethane and like ethers and water, which are employed singly or in a mixture of two or more of them. Examples of basic compound are sodium hydroxide, potassium hydroxide, barium hydroxide and like alkali metal or alkaline earth metal hydroxides.

In carrying out the reaction, the molar amount of basic compound employed is preferably 1–10 times as much as the molar amount of compound of formula (3). The reaction temperature is within the range of 0°–100° C., preferably 50°–100° C., and the reaction time is within the range of 0.5–100 hours, preferably 1–50 hours. These conditions are favorable to the progress of the reaction.

<Step C>

The compounds of formula (5) or formula (6) may be produced by reacting halogenating agent with compounds of formula (3) or formula (4) usually without solvent, or optionally in an inert solvent, respectively. Examples of inert solvent are not specifically limited to, as long as the solvent does not exert an adverse effect on the reaction, but include chloroform, benzene, toluene, xylene, etc. Examples of halogenating agents are thionyl chloride, thionyl bromide, phosphorous oxychloride, phosphorus chloride, phosphorus bromide, phosphorus pentachloride, phosphorus pentabromide, etc. Pyridine or dimethylformamide may be added to accelerate the reaction.

In carrying out the reaction, the molar amount of halogenating agent employed is preferably about 1–100 times as much as the molar amount of compound of formula (3) or formula (4). The reaction temperature is within the range of 0°–200° C., preferably 50–150° C., and the reaction time is within the range of 0.5–100 hours, preferably 0.5–10 hours. These conditions are favorable to the progress of the reaction.

The compound of formula (5) or formula (6) is optionally separated and purified, but may be employed in the following step without purification.

<Step D>

The compound of formula (2a) is produced by reacting compound of formula (5) or formula (6) obtained in step C with protonic acid or Lewis acid without solvent or optionally in the presence of inert solvent.

Examples of inert solvent are not specifically limited to, as long as the solvent does not exert an adverse effect on the reaction, but include nitrobenzene, xylene, dichloromethane, carbontetrachloride, etc. Examples of protonic acid are sulfuric acid, phosphoric acid, polyphosphoric acid, hydrobromic acid, etc. Examples of Lewis acid are aluminium chloride, tin chloride, iron chloride, etc.

In carrying out the reaction, the molar amount of protonic acid or Lewis acid employed is 1–1000 times, preferably 1–100 times as much as the molar amount of compound of formula (5) or (6). The reaction temperature is within the range of 0°–200° C., and the reaction time is within the range of 0.5–50 hours, preferably 0.5–20 hours. These conditions are favorable to the progress of the reaction.

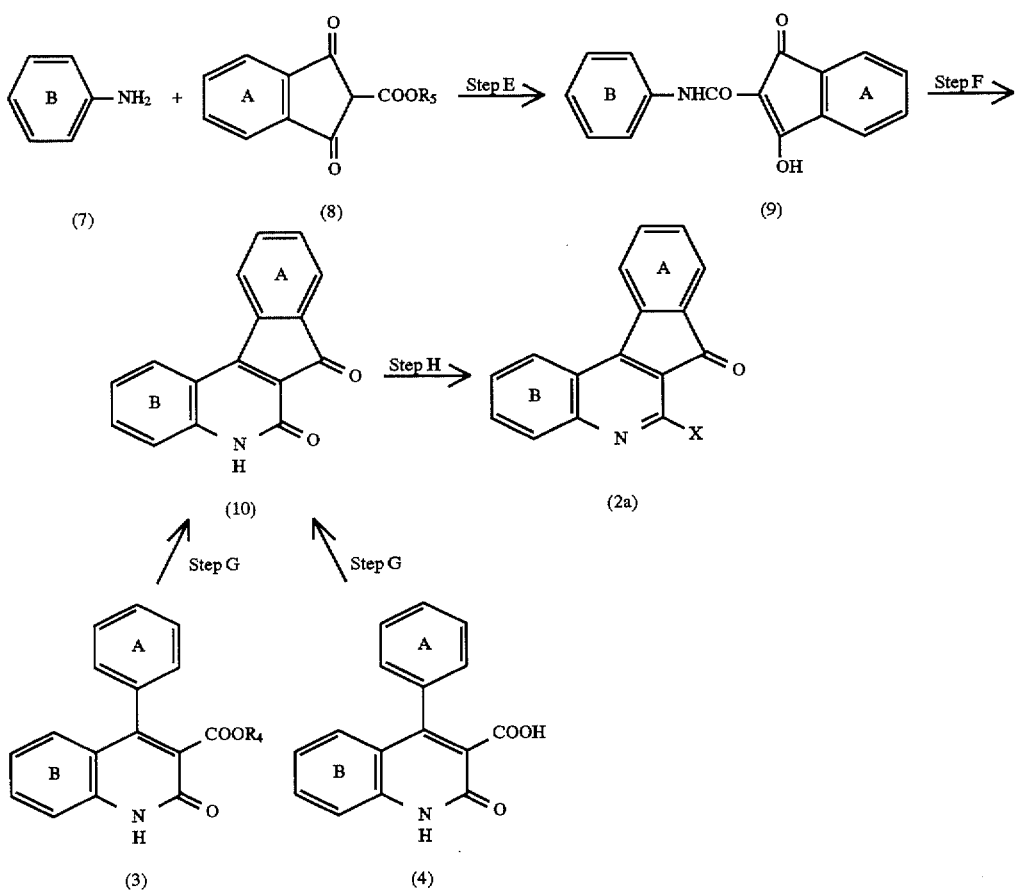

<Reaction formula 3> wherein ring A, ring B, X and $R_4$ are as defined above. $R_5$ represents a lower alkyl group.

<Step E>

The compound of formula (9) is produced by reacting compound of formula (7) with compound of formula (8) usually in a suitable solvent.

Examples of solvent are not specifically limited to, as long as the solvent does not exert an adverse effect on the reaction, but include methanol, ethanol, propanol and like alcohols, benzene, toluene, xylene, dioxane, tetrahydrofuran, etc.

In carrying out the reaction, the molar amount of compound (8) employed is preferably 0.5–2 times as much as the molar amount of compound of formula (7). The reaction temperature is within the range of 20°–150° C., preferably 90°–130° C. The reaction time is within the range of 0.1–50 hours, preferably 0.1–2 hours. These conditions are favorable to the progress of the reaction.

<Step F>

The compound of formula (10) is produced by reacting compound of formula (9) obtained in step E with protonic acid usually without solvent, optionally in the presence of inert solvent.

Examples of inert solvent of the reaction are not specifically limited to, as long as the solvent does not exert an adverse effect on the reaction, but include nitrobenzene, xylene, etc. Examples of protonic acid are sulfuric acid, phosphoric acid, polyphosphoric acid, hydrobromic acid, etc.

In carrying out the reaction, the amount of protonic acid employed is an amount as solvent, preferably 5–15 times as much as the amount of compound of formula (9). The reaction temperature is within the range of 90°–150° C. The reaction time is within the range of 0.5–50 hours, preferably 1–10 hours. These conditions are favorable to the progress of the reaction.

<Step G>

The compound of formula (10) is also produced by reacting compound of formula (3) or (4) with protonic acid usually without solvent, optionally in the presence of inert solvent.

Examples of inert solvent of the reaction are not specifically limited to, as long as the solvent does not exert an adverse effect on the reaction, but include nitrobenzene, xylene, etc. Examples of protonic acid are sulfuric acid, phosphoric acid, polyphosphoric acid, hydrobromic acid, etc.

In carrying out the reaction, the amount of protonic acid employed is an amount as solvent, preferably 5–15 times as much as the amount of compound of formula (3) or (4). The reaction temperature is within the range of 50°–200° C. The reaction time is within the range of 0.5–50 hours, preferably 0.5–10 hours. These conditions are favorable to the progress of the reaction.

<Step H>

The compound of formula (2a) is produced by reacting compound of formula (10) obtained in step F or step G with a halogenating agent usually without solvent, optionally in the presence of inert solvent.

Examples of inert solvent of the reaction are not specifically limited to, as long as the solvent does not exert an adverse effect on the reaction, but include chloroform, benzene, toluene, xylene, etc. Examples of halogenating agent are thionyl chloride, thionyl bromide, phosphorous oxychloride, phosphorus chloride, phosphorus bromide, phosphorus pentachloride, phosphorus pentabromide, etc. Pyridine, dimethylformamide, etc., may be added to accelerate the reaction.

In carrying out the reaction, the molar amount of halogenating agent employed is preferably 1–100 times as much as the molar amount of compound of formula (10). The reaction temperature is within the range of 0°–200° C., preferably 50°–150° C. The reaction time is within the range of 0.5–50 hours, preferably 0.5–10 hours. These conditions are favorable to the progress of the reaction.

The 5-halogenoindeno[2,1-c]isoquinoline derivatives represented by formula (2), which is employed as starting material in reaction formula 1, may be produced according to reaction formula 4 shown below.

<Reaction formula 4>

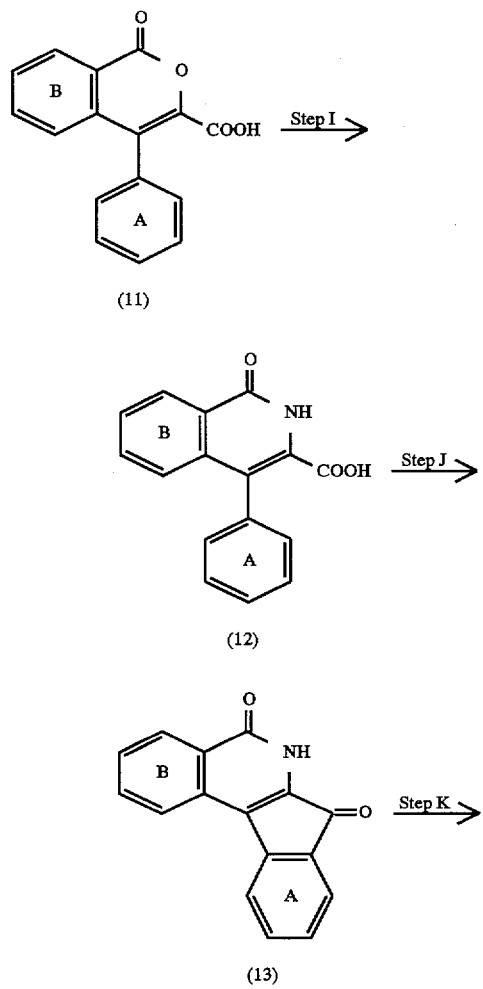

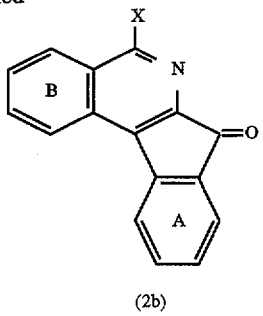

(2b)

wherein ring A, ring B and X are as defined above.
<Step I>
The carboxylic acid of formula (12) is produced by treating compound of formula (11) with ammonia in an inert solvent.

The reaction may be carried out according to a known method disclosed in Bolletino Chimico Farmaceutico, 125, 437 (1986).

In addition, the compound of formula (11) may be synthesized according to the description of Boll. Sedute Accad. Gioenia Sci. Nat. Catania, 6, 606 (1960), or Japanese Unexamined Patent Publication No. 5-132463.

Examples of solvent are not specifically limited to, as long as the solvent does not exert an adverse effect on the reaction, but include methanol, ethanol, propanol and like alcohols, etc.

In carrying out the reaction, the molar amount of ammonia employed is 1–1000 times, preferably 10–100 times as much as the molar amount of compound of formula (11). The reaction temperature is within the range of 0°–100° C., preferably about room temperature, and the reaction time is within the range of 0.5–100 hours, preferably 2–20 hours. These conditions are favorable to the progress of the reaction.
<Step J>
The compound of formula (13) is produced by reacting compound of formula (12) obtained in step I with protonic acid or Lewis acid without solvent or optionally in the presence of inert solvent.

Examples of inert solvent are not specifically limited to, as long as the solvent does not exert an adverse effect on the reaction, but include nitrobenzene, carbon disulfide, nitroparaffin, chloroethylene, dichloromethane, etc. Examples of protonic acid are hydrogen fluoride, sulfuric acid, phosphoric acid, diphosphorous pentaoxide, polyphosphoric acid, etc. Examples of Lewis acid are aluminium chloride, iron chloride, stannic chloride, zinc chloride, boron fluoride, etc.

In carrying out the reaction, the molar amount is 5–15 times in protonic acid and 1–10 times in Lewis acid as much as the molar amount of compound of formula (12). The reaction temperature is within the range of 0°–200° C., and the reaction time is within the range of 0.5–50 hours, preferably 0.5–20 hours. These conditions are favorable to the progress of the reaction.
<Step K>
The compound of formula (2b) is produced by reacting compound of formula (13) obtained in step J with halogenating agent usually without solvent, optionally in the presence of inert solvent.

Examples of inert solvent of the reaction are not specifically limited to, as long as the solvent does not exert an adverse effect on the reaction, but include chloroform, benzene, toluene, xylene, etc. Examples of halogenating agent are thionyl chloride, thionyl bromide, phosphorous oxychloride, phosphorus chloride, phosphorus bromide, phosphorus pentachloride, phosphorus pentabromide, etc. Pyridine, dimethylformamide, etc., may be added to accelerate the reaction.

In carrying out the reaction, the molar amount of halogenating agent employed is preferably 1–100 times as much as the molar amount of compound of formula (13). The reaction temperature is within the range of 0°–200° C., preferably 50°–150° C. The reaction time is within the range of 0.5–50 hours, preferably 0.5–10 hours. These conditions are favorable to the progress of the reaction.

The compounds of the invention and other compounds produced in any of the above-mentioned methods may be isolated and purified by conventional separation and purification means employed in the relevant field of art, for example, by concentration, extraction with solvent, filtration, recrystallization, various chromatographic techniques and so forth.

When the compounds of the invention is employed as medicaments for malignant tumor of mammal, the compound may be made into various pharmaceutical dosage forms according to therapeutic purpose. Examples of pharmaceutical dosage forms are oral preparations, such as tablets, coated tablets, pills, powders, granules, capsules, liquids, suspensions, emulsions, and parenteral preparations such as injections, suppositories, ointments, plasters and so on. Such preparations can be formulated in a manner already known or conventional to those skilled in the art.

When formulated in a form of tablets, employed as carriers are excipients such as lactose, sucrose, sodium chloride, glucose, urea, starch, calcium carbonate, kaolin, crystalline cellulose and silicic acid; binders such as simple syrup, glucose solution, starch solution, gelatin solution, carboxymethyl cellulose, shellac, methyl cellulose, potassium phosphate and polyvinyl pyrrolidone; disintegrators such as dried starch, sodium alginate, agar powder, powdered laminaran, sodium bicarbonate, calcium carbonate, polyoxyethylene sorbitan fatty acid esters, sodium lauryl sulfate, stearic acid monoglyceride, cacao butter, hydrogenated oil; absorption promoters such as quaternary ammonium base, sodium lauryl sulfate; humectants such as glycerine, starch; adsorbent such as starch, lactate, kaolin, bentonite, colloidal silicone dioxide; lubricants such as purified talc, stearic acid salt, borax and polyethylene glycol. Tablets may optionally be formed as tablets to which conventional coating is applied, such as sugar-coated tablets, gelatine-coated tablets, enteric-coated tablets, film-coating tablets, double-layer tablets, milti-layer tablets, etc.

For the formulation of pills, as carrier are employed excipients such as glucose, lactose, starch, cacao butter, hardened vegetable oil, kaolin, talc; binders such as gum arabic powder, tragacanth powder, gelatine; disintegrators such as laminaran, agar.

Capsules may be prepared according to a conventional method, by mixing the compound of the invention with said carriers, followed by filling the mixture in hard gelatin capsule, soft elastic capsule, etc., For the formulation of suppositories, as carriers are employed polyethylene glycol, cacao butter, higher alcohols, higher alcohol esters, gelatine, semi-synthesized glycerides, etc.

When prepared as injections, liquids, emulsion and suspensions are preferably sterile and isotonic to blood. For the formulation of said preparations, employed are diluents such as water, ethanol, macrogol, propyleneglycol, ethoxylated isostearyl alcohol, polyoxylated isostearyl alcohol, polyoxyethylene sorbitane fatty acid esters, etc. To the medicinal preparations are added not only sodium chloride, glucose and glycerin in an enough amount to prepare isotonic solution, but also conventional solubilizer, buffers, local anesthetic, etc.

Ointments may be prepared in a conventional manner by optionally blending to the compound of the invention base, stabilizer, wetting agent, preservative etc., and the resulting composition is admixed to give ointment preparations. Examples of base are liquid paraffin, white petrolatum, white beeswax, paraffin, etc. Examples of preservative are methyl parahydroxybenzoate, ethyl parahydroxybenzoate, propyl parahydroxybenzoate, etc.

Plasters are prepared by applying said ointments, pastes, creams, gels etc. to conventional supports. Examples of supports are suitably woven fabrics and unwoven fabrics made of cotton, staple fiber or some other chemical fiber, films or foamed sheets made of plasticized polyvinyl chloride, polyethylene, polyurethane, etc.

Coloring agent, preservatives, perfumes, flavors, sweeteners, and other medicaments may optionally be added to the medical formulations.

The amount of the compounds of the invention in medical formulations are not specifically limited to, but usually include 1–70% by weight of the medicinal preparations.

The way of administration of said medicinal preparations is not specifically limited to, but suitably determined according to the type of preparations, age, sex and other factors of patients, severity of disorder, etc. For example, tablets, pills, liquids, suspensions, emulsions, granules, capsules are orally administered. Injections are intravenously administered singly or in a mixture with conventional additives, such as glucose, amino acids, etc. Injections may be intramuscularly, intracutaneously, subcutaneously or intraperitoneally administered in a single form. Suppositories are administered in rectum. Ointments are applied to skin, tunica mucosa oris, etc.

The amount of the compound of the present invention to be incorporated into each of the dosage units varies with the symptoms of the patient or with the type of the preparations. The preferable amount per administration unit is about 1 to 1,000 mg for oral preparations, about 0.1 to 500 mg for injections, or about 5 to 1,000 mg for suppositries. The dosage per day of the drug in the above dosage form is variable with the symptoms, body weight, age, sex and other factors of the patient, but usually ranges from about 0.1 to 5,000 mg, preferably from about 1 to 1,000 mg for human adult. The preparation is preferably administered in a single dose or in two to four divided doses.

Examples of malignant tumor treated by administering preparations containing the compounds of the invention are not specifically limited to, but include head and neck cancer, esophageal carcinoma, gastric cancer, colon cancer, rectum cancer, cancer of liver, gallbladder cancer or cholangioma, pancreatic cancer, pulmonary cartinoma, breast cancer, ovarian cancer, bladder cancer, prostatic cancer, testicular tumor, osteochondroma, malignant lymphoma, leukemia, cervical cancer, skin carcinoma, brain tumor, etc.

Best Mode for Carrying out the Invention

Reference examples, examples, pharmacological test examples and dosage form examples of the invention are shown below.

<Reference example 1>

Synthesis of 1,2-dihydro-4-(3,4-methylenedioxyphenyl)-2-oxo-3-quinoline carboxylic acid A mixture of 1,2-dihydro-4-(3,4-methylenedioxyphenyl)-2-oxo-3-quinoline carboxylic acid ethyl ester (40 g, 118.6 mmol), methanol (200 ml), water (300 ml) and potassium hydroxide (33.3 g, 593.5 mmol) was refluxed with heat for 40 hours. To the reaction mixture was added 110 ml of 6N-HCl to acidify the mixture to obtain a precipitated crystal by filtration. The crystal obtained was washed with diethylether to give 35 g (yield: 95.4%) of the title compound.

m.p.: 247°–250° C. (decomp.)

$^1$H-NMR(DMSO-d$_6$) δ: 7.45(1H, m), 7.35(1H, d, J=8 Hz), 7.13(1H, m), 7.06(1H, d, J=8 Hz), 6.98(1H, d, J=8 Hz), 6.87(1H, s), 6.76(1H, d, J=8 Hz), 6.08(2H, s).

IR(KBr)cm$^{-1}$: 3440, 1646, 1577, 1486, 1441, 1395, 1238, 1039.

<Reference example 2>

Synthesis of 6-chloro-9,10-methylenedioxy-7H-indeno[2,1-c]quinoline-7-on

A mixture of 1,2-dihydro-4-(3,4-methylenedioxyphenyl)-2-oxo-3-quinoline carboxylic acid obtained in reference example 1 (10 g, 32.3 mmol) and phosphorous oxychloride (100 ml, 1.07 mol) was refluxed with heat for 4 hours. The reaction mixture was distilled to dryness and washed with n-hexane several times. To the residue obtained was added 50 g of polyphosphoric acid, and the mixture was heated at 90° C. for 2 hours. The reaction mixture was poured into ice water to filtrate a crystal precipitated. The crystal obtained was dissolved in tetrahydrofuran to filter off undissolved substances and purified by silica gel column chromatography (eluent: chloroform) to give 6.0 g (yield 59.9%) of the title compound.

m.p.: 265°–270° C.

$^1$H-NMR(CDCl$_3$) δ: 8.34(1H, d, J=8 Hz), 8.04(1H, d, J=8 Hz), 7.84(1H, d-d, J=8,7 Hz), 7.66(1H, d-d, J=8,7 Hz), 7.58(1H, s), 7.23(1H, s), 6.17(2H, s).

IR(KBr)cm$^{-1}$: 3450, 1713, 1556, 1504, 1478, 1420, 1384, 1335, 1266, 1037.

<Reference example 3>

Synthesis of 1,2-dihydro-4-phenyl-2-oxo-3-quinoline carboxylic acid

A mixture of 1,2-dihydro-4-phenyl-2-oxo-3-quinoline carboxylic acid ethyl ester (5 g, 17 mmol), ethanol (20 ml), water (40 ml) and potassium hydroxide (5 g, mmol) was refluxed with heat for 1.5 hours. To the reaction mixture was added 60 ml of 2N-HCl to acidify the mixture to obtain a precipitated crystal by filtration. The crystal obtained was recrystallized from ethanol to give 4.2 g (yield: 92.9%) of the title compound.

m.p.: 246°–254° C. (decomp.)

$^1$H-NMR(DMSO-d$_6$) δ: 13.10(1H, brs), 12.28(1H, s), 7.60–7.05(9H, m),

IR(KBr)cm$^{-1}$: 3000, 2970, 2950, 2880, 2850, 2840, 2790, 1699, 1653, 1608, 1598, 1557, 1506, 1488, 1435, 1411, 1262, 1100, 753, 709, 591.

<Reference example 4>

Synthesis of 5H-indeno[2,1-c]quinoline-6,7-dion

A mixture of 1,2-dihydro-4-phenyl-2-oxo-3-quinoline carboxylic acid obtained in reference example 3 (2 g, 7.5 mmol) and polyphosphoric acid (20 g) was reacted at 130° C. for 4 hours. The reaction mixture was poured into ice water to obtain a crystal precipitated by filtration. The crystal obtained was reprecipitated with methanol to give 1.7 g (yield 91.2%) of the title compound.

m.p.: >290° C.

$^1$H-NMR(DMSO-d$_6$) δ: 12.12(1H, brs), 8.55(1H, d, J=8 Hz), 8.40(1H, d, J=8 Hz), 7.78–7.33(6H, m).

IR(KBr)cm$^{-1}$: 2860, 1724, 1652, 1618, 1601, 1585, 1503, 1484, 1404, 763, 743, 576.

<Reference example 5>

Synthesis of 3-methyl-5H-indeno[2,1-c]quinoline-6,7-dion

A mixture of 1,2-dihydro-4-phenyl-7-methyl-2-oxo-3-quinoline carboxylic acid ethyl ester (2.5 g, 8.1 mmol) and conc. sulfuric acid (20 ml) was stirred with heat at 95° C. for 10 hours. The reaction mixture was poured into ice water to obtain a crystal precipitated by filtration. The crystal obtained was washed with water and methanol in this sequence to give 1.5 g (yield 70.6 of the title compound.

m.p.: >290° C.

$^1$H-NMR(DMSO-d$_6$) δ: 12.03(1H, brs), 8.41(1H, d, J=8 Hz), 8.36(1H, d, J=7 Hz), 7.70–7.17(5H, m), 2.44(3H, s)

IR(KBr)cm$^{-1}$: 3440, 1711, 1643, 1599, 1580, 1543, 1481, 1465, 1437, 1404.

<Reference example 6>

Synthesis of 6-chloro-3-methyl-7H-indeno[2,1-c]quinoline-7-on

A mixture of 3-methyl-5H-indeno[2,1-c]quinoline-6,7-dion obtained in reference example 5 (700 mg, 2.7 mmol) and phosphorous oxychloride (10 ml, 107 mmol) was refluxed with heat for 1.5 hours. The reaction mixture was distilled to dryness. To the residue was added water to obtain a crystal precipitated by filtration. The crystal obtained was washed with water and dissolved in chloroform to filter off undissolved substances. Recrystallization from benzene to give 550 mg (yield 73.4%) of the title compound.

m.p.: 208°–211° C.

$^1$H-NMR(CDCl$_3$) δ: 8.38(1H, d, J=9 Hz), 8.13(1H, d, J=7 Hz), 7.85(1H, s), 7.80(1H, d, J=6 Hz), 7.64(1H, d-d-d, J=8,8,1 Hz), 7.56–7.50(2H, m), 2.60(3H, s).

IR(KBr)cm$^{-1}$: 1718, 1623, 1557, 1494, 1460, 1413, 1064, 915, 867, 755, 715.

<Reference example 7>

Synthesis of 1,3-dioxo-3,-methoxy-2-indancarboxyanilide

To a suspension of 2-ethoxycarbonyl-1,3-indandione (2.7 g, 12.5 mmol) in toluene (100 ml) was added m-anisidine (1.7 g, 13.8 mmol) and the mixture was refluxed with heat for 0.5 hour. About half amount of the solvent was distilled off to obtain a crystal precipitated by filtration. The crystal obtained was recrystallized from ethanol to give 1.7 g (yield 46.0%) of the title compound.

m.p.: 128°–138° C.

$^1$H-NMR(CDCl$_3$) δ: 9.52(1H, brs), 7.70–7.55(4H, m), 7.31(1H, d, J=8 Hz), 7.17(1H, d-d, J=2, 2 Hz), 7.10–6.74 (2H, m), 3,84(1H, s).

IR(KBr)cm$^{-1}$: 1658, 1604, 1584, 1563, 1537, 1496, 1455, 1416.

<Reference example 8>

Synthesis of 3-methoxy-5H-indeno[2,1-c]quinoline-6,7-dion

A mixture of 1,3-dioxo-3'-methoxy-2-indancarboxyanilide (1.6 g, 5.4 mmol) obtained in reference example 7 and polyphosphoric acid (18 g) was reacted at 120° C. for 1.5 hours. The reaction mixture was poured into ice water to obtain a crystal precipitated by filtration. The crystal obtained was washed with tetrahydrofuran to give 1.0 g (yield 66.6%) of the title compound.

m.p.: 236°–246° C. (decomp.)

$^1$H-NMR(DMSO-d$_6$) δ: 8.48(1H, d, J=9 Hz), 8.35(1H, d, J=7 Hz), 7.71–7.55(3H, m), 6.99–6.92(2H, m), 3.90(3H, s)

IR(KBr)cm$^{-1}$: 1705, 1640, 1621, 1585, 1480, 1415, 1394

<Reference example 9>

Synthesis of 6-chloro-3-methoxy-7H-indeno[2,1-c]quinoline-7-on

A mixture of 3-methoxy-5H-indeno[2,1-c]quinoline-6,7-dion (550 ml, 2.0 mmol) obtained in reference example 8 and phosphorous oxychloride (20 ml, 214 mmol) was refluxed with heat in the presence of catalytic amount of N,N-dimethylformamide for 4 hours. The reaction mixture was distilled to dryness. To the residue was added water to obtain a crystal precipitated by filtration. The crystal obtained was dissolved in chloroform to filter off undissolved substances. Recrystallization from benzene gave 460 mg (yield 78.4%) of the title compound.

m.p.: 261°–266° C.

$^1$H-NMR(CDCl$_3$) δ: 8.39(1H, d, J=9 Hz), 8.11(1H, d, J=8 Hz), 7.81(1H, m), 7.64(1H, d-d-d, J=8,8,1 Hz), 7.53(1H, m), 7.41(1H, d, J=2 Hz), 7.33(1H, d-d, J=9,2 Hz), 4.00(3H, s).

IR(KBr)cm$^{-1}$: 1706, 1618, 1564, 1496, 1474, 1464, 1428, 1208, 1186, 1157, 1122, 1060, 1012.

<Reference example 10>

Synthesis of 1,2-dihydro-7-methoxy-4-phenyl-2-oxo-3-quinoline carboxylic acid ethyl ester A mixture of 2-amino-4-methoxybenzophenone (20 g, 88 mmol), diethylmalonate (26.7 ml, 176 mmol), 1,8-diazabicyclo[5,2,0]-undeca-7-en (DBU) (0.66 ml, 4.4 mmol) was stirred with heat at 160° C. for 2 hours. The reaction mixture was cooled by air. To the cooled mixture was added ethanol (30 ml) to obtain a precipitated crystal by filtration. The crystal obtained was washed with ethanol to give 25.7 g (yield: 90.2%) of the title compound.

m.p.: 175°–177° C.

$^1$H-NMR(CDCl$_3$) δ: 12.60(1H, brs), 7.48–7.35(5H, m), 7.18(1H, d, J=9 Hz), 6.91(1H, d, J=3 Hz), 6.72(1H, d-d, J=9,3 Hz), 4.08(2H, q, J=7 Hz), 3.90(3H, s), 0.97(3H, t, J=7 Hz)

IR(KBr)cm$^{-1}$: 2980, 2940, 1735, 1642, 1597, 1516, 1238, 1213, 1094.

<Reference example 11>

Synthesis of 1,2-dihydro-7-methoxy-4-phenyl-2-oxo-3-quinoline carboxylic acid

A 3.0 g of 1,2-dihydro-7-methoxy-4-phenyl-2-oxo-3-quinoline carboxylic acid ethyl ester obtained in reference example 10 was reacted and treated in the same procedure as reference example 1, and washed with ethanol to give 2.7 g (yield: 99.0%) of the title compound.

m.p.: 292°–294° C.

$^1$H-NMR(DMSO-d$_6$) δ: 13.23(1H, s), 12.25(1H, s), 7.54–7.44(3H, m), 7.31–7.27(2H, m), 6.99–6.90(2H, m), 6.80(1H, m), 3.83(3H, s).

IR(KBr)cm$^{-1}$: 3170, 1731, 1625, 1476, 1403, 1243, 1212, 847.

<Reference example 12>

Synthesis of 6-chloro-3-methoxy-7H-indeno[2,1-c]quinoline-7-on (another method)

Said 1,2-dihydro-7-methoxy-4-phenyl-2-oxo-3-quinoline carboxylic acid obtained in reference example 11 was reacted and treated in the same procedure as reference example 2 to give the title compound. The physicochemical properties of the compound obtained corresponded to those of reference example 9.

<Reference example 13>

Synthesis of 6-chloro-3-hydroxy-7H-indeno[2,1-c]quinoline-7-on

A mixture of 6-chloro-3-methoxy-7H-indeno[2,1-c]quinoline-7-on (10.0 g, 33.8 mmol) obtained in reference example 9 and 100 ml of conc. sulfuric acid was stirred with heat at 160° C. for 2 hours. The reaction mixture was poured into ice water to obtain a crystal precipitated by filtration. The crystal obtained was washed with water and ethanol in this sequence to give 8.5 g (yield 89.4%) of the title compound.

m.p.: >300° C.

$^1$H-NMR(DMSO-d$_6$) δ: 11.18(1H, brs), 8.66(1H, d, J=9 Hz), 8.43(1H, d, J=8 Hz), 7.77–7.59(3H, m), 7.35(1H, d-d, J=9,2 Hz), 7.23(1H, d, J=2 Hz).

IR(KBr)cm$^{-1}$: 3110, 1711, 1623, 1610, 1461, 1435, 1398, 1179, 1067, 750.

<Reference example 14>

Synthesis of 3-benzyloxy-6-chloro-7H-indeno[2,1-c]quinoline-7-on

To a suspension of 6-chloro-3-hydroxy-7H-indeno[2,1-c]quinoline-7-on (500 mg, 1.8 mmol) obtained in reference example 13 and potassium carbonate (300 mg, 2.1 mmol) in N,N-dimethylformamide (5 ml) was added benzylchloride (247 mg, 2.0 mmol) and the mixture was stirred at 90° C. for 3 hours. The reaction mixture was poured into ice water to obtain a crystal precipitated by filtration. The crystal obtained was washed with water and 2-propanol in this sequence to give 610 mg (yield 92.4%) of the title compound.

m.p.: 212°–214° C.

$^1$H-NMR(CDCl$_3$) δ: 8.40(1H, d, J=9.5 Hz), 8.10(1H, d, J=7.5 Hz), 7.80(1H, d, J=7.5 Hz), 7.67–7.31(9H, m), 5.24 (2H, s)

IR(KBr)cm$^{-1}$: 3090, 1711, 1623, 1570, 1461, 1435, 1397, 1179, 1067, 750.

<Reference example 15>

Synthesis of 1,2-dihydro-4-phenyl-1-oxo-3-isoquinoline carboxylic acid

To a methanol (50 ml) solution of 4-phenylisocoumaline-3-carboxylic acid (36.2 g, 136 mmol) was added 100 ml of saturated ammonia in methanol solution, and the mixture was stirred at room temperature for 8 hours. The mixture was distilled to remove solvent. To the residue was added 300 ml of methanol and 100 ml of 4N-hydrochloride in ethyl acetate solution to acidify the mixture. Solvent was removed by distillation. Water was added to the residue to obtain a crystal precipitated by filtration. The crystal obtained was recrystallized from ethanol-water to give 32.0 g (yield: 88.7%) of the title compound.

m.p.: >300° C.

$^1$H-NMR(DMSO-$d_6$) δ: 13.53(1H, brs), 11.11(1H, brs), 8.32(1H, d, J=8 Hz), 7.72–7.26(7H, m), 7.10(1H, d, J=8 Hz).

IR(KBr)cm$^{-1}$: 3160, 1704, 1656, 1643, 1622, 1606, 1598, 1468, 1446, 1307, 761, 706

<Reference example 16>

Synthesis of 6H-indeno[2,1-c]isoquinoline-5,7-dion

A mixture of 1,2-dihydro-4-phenyl-1-oxo-3-isoquinoline carboxylic acid (32 g) obtained in reference example 15 and polyphosphoric acid (300 g) was reacted at 100° C. for 5 hours. The reaction mixture was poured into ice water to obtain a crystal precipitated by filtration. The crystal obtained was washed with ethyl acetate to give 26.6 g (yield 89.2%) of the title compound.

m.p.: >300° C.

$^1$H-NMR(DMSO-$d_6$) δ: 12.18(1H, brs), 8.40–8.35(2H, m), 7.94–7.88(2H, m), 7.73(1H, d-d, J=8,8 Hz), 7.54–7.46 (2H, m), 7.24(1H, d-d, J=7,7 Hz).

IR(KBr)cm$^{-1}$: 3060, 1716, 1681, 1645, 1620, 1604, 1598, 1588, 1462, 1328, 716.

<Reference example 17>

Synthesis of 5-chloro-7H-indeno[2,1-c]isoquinoline-7-on

A mixture of 6H-indeno[2,1-c]isoquinoline-5,7-dion obtained in reference example 16 (26.6 g, 108 mmol) and phosphorous oxychloride (300 ml) was refluxed with heat in the presence of 1 ml of N,N-dimethylformamide for 2 hours. The reaction mixture was distilled to dryness. To the residue was added ice water to obtain a crystal precipitated by filtration. The crystal obtained was washed with water and recrystallized from toluene to give 22.5 g (yield 78.7%) of the title compound.

m.p.: 242°–244° C.

$^1$H-NMR(CDCl$_3$) δ: 8.51–8.47(2H, m), 7.99–7.82(3H, m), 7.74(1H, d, J=7 Hz), 7.59(1H, d-d, J=8,8 Hz), 7.40(1H, d-d, J=8,7 Hz ).

IR(KBr)cm$^{-1}$: 1738, 1722, 1615, 1602, 1461, 1412, 1347, 1253, 765, 713, 682, 616.

<Reference example 18>

The following compounds were synthesized by employing compounds of reference examples 1–17.

* 2,6-dichloro-7H-indeno[2,1-c]quinoline-7-on m.p.: 282°–284° C.

$^1$H-NMR(CDCl$_3$) δ: 8.46(1H, d, J=8 Hz), 8.11(1H, d, J=7 Hz), 8.03(1H, d, J=9 Hz), 7.84–7.79(2H, m), 7.69(1H, d-d-d, J=8,8,1 Hz), 7.57(1H, d-d, J=7,7 Hz).

* 6-chloro-2-methoxy-7H-indeno[2,1-c]quinoline-7-on m.p.: 261°–262° C.

$^1$H-NMR(CDCl$_3$) δ: 8.06(1H, d, J=8 Hz), 8.00(1H, d, J=9 Hz), 7.82(1H, d, J=7 Hz), 7.68–7.50(4H, m), 4.06(3H, s).

* 6-chloro-2-nitro-7H-indeno[2,1-c]quinoline-7-on m.p.: >300° C.

$^1$H-NMR(CDCl$_3$) δ: 9.47(1H, d, J=2 Hz), 8.64(1H, d-d, J=9,2 Hz), 8.25(1H, d, J=8 Hz), 8.24(1H, d, J=9 Hz), 7.88(1H, d, J=7 Hz), 7.78(1H, d-d-d, J=8,8,1 Hz), 7.64(1H, d-d, J=8,8 Hz).

* 6-chloro-2,3-methylenedioxy-7H-indeno[2,1-c]quinoline-7-on m.p.: >300° C.

$^1$H-NMR(CDCl$_3$) δ: 8.02(1H, d, J=8 Hz), 7.81(1H, d, J=7 Hz), 7.72(1H, s), 7.64(1H, d-d-d, J=8,8,1 Hz), 7.52(1H, d-d, J=8,8 Hz), 7.37(1H, s), 6.23(2H, s).

* 6-chloro-2,3-dimethoxy-7H-indeno[2,1-c]quinoline-7-on m.p.: 300°–302° C.

$^1$H-NMR(CDCl$_3$) δ: 8.00(1H, d, J=7 Hz), 7.82(1H, d, J=7 Hz), 7.65(1H, d-d, J=8,8 Hz), 7.61(1H, s), 7.52(1H, d-d, J=8,7 Hz), 7.41(1H, s), 4.14(3H, s), 4.07(3H, s).

* 6-chloro-3-fluoro-7H-indeno[2,1-c]quinoline-7-on m.p.: 257°–259° C.

$^1$H-NMR(CDCl$_3$) δ: 8.55(1H, m), 8.12(1H, d, J=7 Hz), 7.84(1H, d, J=7 Hz), 7.76–7.47(4H, m).

* 6-chloro-3,9-dimethoxy-7H-indeno[2,1-c]quinoline-7-on m.p.: 298°–300° C.

$^1$H-NMR(CDCl$_3$) δ: 8.31(1H, d, J=9 Hz), 7.98(1H, d, J=9 Hz), 7.37(1H, d, J=3 Hz), 7.33(1H, d, J=3 Hz), 7.29(1H, d-d, J=9,3 Hz), 7.08(1H, d-d, J=8,3 Hz), 3.99(3H, s), 3.94(3H, s).

* 3,6-dichloro-7H-indeno[2,1-c]quinoline-7-on m.p.: 250°–252° C.

$^1$H-NMR(CDCl$_3$) δ: 8.40(1H, d, J=9 Hz), 8.07(1H, d, J=9 Hz), 8.05(1H, s), 7.80(1H, d, J=7 Hz), 7.69–7.52(3H, m).

* 3-benzyloxy-6-chloro-9,10-methylenedioxy-7H-indeno[2,1-c]quinoline-7-on m.p.: 241°–243° C.

$^1$H-NMR(CDCl$_3$) δ: 8.19(1H, d, J=9 Hz), 7.60–7.31(8H, m), 7.19(1H, s), 6.15(2H, s), 5.21(2H, s).

* 6-chloro-3-methoxy-9,10-methylenedioxy-7H-indeno[2,1-c]quinoline-7-on m.p.: >300° C.

$^1$H-NMR(CDCl$_3$) δ: 8.22(1H, d, J=9 Hz), 7.53(1H, s), 7.36(1H, d, J=3 Hz), 7.30(1H, d, J=3 Hz), 7.23(1H, s). 6.16(2H, s), 3.98(3H, s).

* 6-chloro-8-methoxy-7H-indeno[2,1-c]quinoline-7-on m.p.: 259°–260° C.

$^1$H-NMR(CDCl$_3$) δ: 8.48(1H, d, J=8 Hz), 8.08(1H, d, J=8 Hz), 7.84(1H, d-d-d, J=8,7,1 Hz), 7.77(1H, d, J=8 Hz), 7.67(1H, d-d-d, J=8,7,1 Hz), 7.60(1H, d-d, J=9,8 Hz), 7.09(1H, d, J=9 Hz), 4.04(3H, s).

* 6-chloro-8-hydroxy-7H-indeno[2,1-c]quinoline-7-on m.p.: 240°–241° C.

$^1$H-NMR(CDCl$_3$) δ: 8.83(1H, s), 8.46(1H, d, J=9 Hz), 8.09(1H, d, J=9 Hz), 7.88(1H, d-d-d, J=7,7,1 Hz), 7.73–7.65 (2H, m), 7.52(1H, d-d, J=9,7 Hz), 7.03(1H, d, J=9 Hz),

* 6-chloro-9-methoxy-7H-indeno[2,1-c]quinoline-7-on m.p.: 210°–212° C.

$^1$H-NMR(CDCl$_3$) δ: 8.39(1H, d, J=8 Hz), 8.04–7.97(2H, m), 7.83(1H, d-d-d, J=9,7,1 Hz), 7.65(1H, d-d-d, J=8,7,1 Hz), 7.29(1H, d, J=3 Hz) 7.07(1H, d-d, J=8,3 Hz), 3.93(3H, s),

* 6-chloro-10-methoxy-7H-indeno[2,1-c]quinoline-7-on m.p.: 255°–256° C.

$^1$H-NMR(CDCl$_3$) δ: 8.43(1H, d, J=9 Hz), 8.08(1H, d, J=9 Hz), 7.86(1H, d-d-d, J=9,7,1 Hz), 7.76(1H, d, J=8 Hz), 7.69(1H, d-d-d, J=8,7,1 Hz), 7.65(1H, d, J=2 Hz) 6.94(1H, d-d, J=8,2 Hz), 3.99(3H, s),

* 6-chloro-10-hydroxy-7H-indeno[2,1-c]quinoline-7-on
m.p.: >300° C.

$^1$H-NMR(DMSO-d$_6$) δ: 8.64(1H, d, J=8 Hz), 8.05–7.81 (4H, m), 7.63(1H, d, J=8 Hz), 6.95(1H, d-d, J=8,2 Hz).

* 2-aza-1-chloro-13H-dibenzo[c,i]fluorene-13-on
m.p.: 258°–261° C.

$^1$H-NMR(CDCl$_3$) δ: 9.00(1H, d, J=8 Hz), 8.53(1H, d, J=9 Hz), 8.22(1H, d, J=9 Hz), 8.09(1H, d, J=8 Hz), 8.03(1H, d, J=9 Hz), 7.81(1H, d, J=8 Hz), 7.71–7.47(4H, m).

EXAMPLE 1

Synthesis of 6-(((dimethylamino)ethyl)amino)-3-methoxy-7H-indeno[2,1-c]quinoline-7-on
(compound 1)

To a suspension of 6-chloro-3-methoxy-7H-indeno[2,1-c]quinoline-7-on obtained in reference example 9 (2 g, 6.8 mmol) in pyridine (20 ml) was added N,N-dimethylethylenediamine (3 g, 33.8 mmol), and the mixture was stirred with heat at 100° C. for 24 hours. The reaction mixture was distilled to dryness. To the residue was added water and chloroform for extraction. The chloroform layer was dried over magnesium sulfate and evaporated. The residue was purified by silica gel column chromatography (eluent; chloroform:ethanol=10:1(v/v)) and crystallized from ethanol to give 1.3 g (yield 55.3%) of title compound 1. The physicochemical properties thereof are shown in table 1.

The compound obtained was dissolved in a mixture of chloroform-methanol to filter off undissolved substances. The filtrate was acidified with 4N-hydrochloride in ethyl acetate to collect a crystal precipitated. The crystal obtained was dried under reduced pressure to give a salt of compound 1 (compound 1-a) quantitatively. Physicochemical properties thereof were shown in table 1.

EXAMPLE 2

Synthesis of 6-(((dimethylamino)ethyl)amino)-3-fluoro-7H-indeno[2,1-c]quinoline-7-on
dihydrochloride (compound 2)

To a suspension of 6-chloro-3-fluoro-7H-indeno[2,1-c]quinoline-7-on (860 mg, 3.0 mmol) in pyridine (10 ml) was added N,N-dimethylethylenediamine (800 mg, 9.0 mmol), and the mixture was stirred with heat at 90° C. for 12 hours. The reaction mixture was distilled to dryness. To the residue was added water and chloroform for extraction. The chloroform layer was dried over magnesium sulfate and evaporated. The residue was purified by silica gel column chromatography (eluent; chloroform:ethanol=10:1(v/v)). The purified material was dissolved in 20 ml of tetrahydrofuran. To the the solution was added 4N-hydrochloride/dioxane (2 ml) and the mixture was concentrated under reduced pressure. The residue obtained was crystallized from diethylether to give 420 mg (yield 34.3%) of title compound. The physicochemical properties thereof are shown in table 1.

EXAMPLE 3

Synthesis of 6-(((dimethylamino)ethyl)amino)-3-hydroxy-7H-indeno[2,1-c]quinoline-7-on
(compound 3)

To a solution of 6-(((dimethylamino)ethyl)amino)-3-methoxy-7H-indeno[2,1-c]quinoline-7-on obtained in example 1 (3 g, 8.6 mmol) in acetic acid (40 ml) was added 47% aqueous hydrobromic acid (40 ml), and the mixture was refluxed with heat for 60 hours. The reaction mixture was distilled to dryness. To the residue was added water and the solution was adjusted to a pH of about 8 with aqueous ammonia, and subsequently extracted with chloroform. The chloroform layer was dried over magnesium sulfate and evaporated. The residue was purified by silica gel column chromatography (eluent; chloroform:methanol:water=8:3:1 (v/v/v)) and crystallized from cyclohexane to give 2.1 g (yield: 73.0%) of title compound. The physicochemical properties thereof are shown in table 1.

The compound obtained was dissolved in a mixture of chloroform-methanol to filter off undissolved substances. The filtrate was acidified with 4N-hydrochloride in ethyl acetate to collect a crystal precipitated. The crystal obtained was dried under reduced pressure to give a salt of compound 3 (compound 3-a, yield=89.4%). Physicochemical properties thereof were shown in table 1.

EXAMPLE 4

Synthesis of 6-(((dimethylamino)ethyl)amino)-3-(pivaloyloxy)-7H-indeno[2,1-c]quinoline-7-on
(compound 4)

To a solution of 6-(((dimethylamino)ethyl)amino)-3-hydroxy-7H-indeno[2,1-c]quinoline-7-on obtained in example 3 (100 mg, 0.3 mmol) in dichloromethane (10 ml) was added 4-dimethylaminopyridine (100 mg, 0.8 mmol) and pivaloyl chloride (37 μl, 0.3 mmol), and the mixture was stirred at room temperature for 3 hours. To the reaction mixture was added water to wash the organic layer, which was dried over magnesium sulfate and evaporated. The residue was purified by silica gel column chromatography (eluent; chloroform:ethanol=10:1(v/v)) and crystallized from hexane to give 105 mg (yield: 80.0%) of title compound. The physicochemical properties thereof are shown in table 1.

EXAMPLE 5

Synthesis of 6-(((dimethylamino)ethyl)amino)-3-hydroxy-4-nitro-7H-indeno[2,1-c]quinoline-7-on
(compound 5)

A mixture of 6-(((dimethylamino)ethyl)amino)-3-hydroxy-7H-indeno[2,1-c]quinoline-7-on obtained in example 3 (100 mg, 0.3 mmol), conc. sulfuric acid (1 ml) and nitric acid (1 ml) was stirred at 5° C. for 2 hours. The reaction mixture was poured into ice water, and a crystal precipitated was collected by filtration. The crystal obtained was purified by silica gel column chromatography (eluent; a lower layer of chloroform:methanol:water=9:3:1(v/v/v)) and crystallized from ethanol-diethylether to give 60 mg (yield: 52.9%) of title compound. The physicochemical properties thereof are shown in table 1.

EXAMPLE 6

Synthesis of 6-((aminoethyl)amino)-3-hydroxy-7H-indeno[2,1-c]quinoline-7-on-dihydrochloride
(compound 59)

A 20 ml of conc. hydrochloric acid was added to compound 56 (1.1 g) prepared in the same procedure as example 1, and the resulting mixture was reacted at external temperature of 100° C. for 12 hours. After the reaction, isopropanol was added to the mixture. The resulting mixture was allowed to cool to collect a crude crystal precipitated by filtration. The crude crystal obtained was subjected to high porous polymer gel column chromatography (MCI gel; Mitsubishi Chemical Co., Ltd.) and eluted with a solvent mixture (methanol:water=1:1 containing 1 drop of conc. hydrochloric acid). Eluted fractions were concentrated under reduced pressure. A crystal precipitated was filtrated, washed with ethanol and dried under reduced pressure to give 524 mg (yield: 63.7%) of title compound.

EXAMPLE 7

Synthesis of 6-(((methylamino)ethyl)amino)-3-hydroxy-7H-indeno[2,1-c]quinoline-7-on-trihydrochloride (compound 60)

A mixture of conc. hydrochloric acid-dioxane (10 ml—10 ml) was added to compound 57 (1.0 g) prepared in the same procedure as example 1, and the resulting mixture was reacted at external temperature of 100° C. for 3 hours. After the reaction, the mixture was concentrated under reduced pressure. To the residue was again added 10 ml of conc. hydrochloric acid, and the resulting mixture was reacted at external temperature of 100° C. for 2 hours. After the reaction, 30 ml of isopropanol was added to the mixture to collect a crude crystal precipitated by filtration. The crude crystal obtained was dissolved in water. To the solution was added 0.5 ml of conc. hydrochloric acid and 30 ml of isopropanol, and the mixture was stirred on ice-cooling for crystallization to give 560 mg (yield: 68.8%) of title compound.

EXAMPLE 8

Synthesis of 6-(((dimethylaminooxide)ethyl)amino)-3-hydroxy-7H-indeno[2,1-c]quinoline-7-on.dihydrochloride (compound 61)

Compound 53 (2.0 g) prepared in the same procedure as example 1 was dissolved in 10 ml of chloroform. After stirring the solution on ice-cooling, to the solution was added a chloroform (10 ml) solution of m-chloroperbenzoic acid (1.2 g), and the resulting mixture was reacted at room temperature for 3 hours. The reaction product was purified by alumina column chromatography (eluent; chloroform:methanol=40:1) to give 6-((  (dimethylaminooxide)ethyl)amino)-3-benzyloxy-7H-indeno[2,1-c]quinoline-7-on. To the compound was added 7.5 ml of conc. hydrochloric acid, and the mixture was reacted at external temperature of 100° C. for 1.5 hours. After the reaction, 12 ml of ethanol was added to the mixture, and the resulting mixture was allowed to cool to collect a crude crystal precipitated by filtration. The crude crystal obtained was suspended in 15 ml of ethanol. The suspension was stirred with heat and allowed to cool to collect a crystal by filtration. The crystal obtained was further suspended in 15 ml of dichloromethane and stirred with heat. The suspension was allowed to cool to collect a crystal by filtration giving 1.34 g (yield: 84.1%) of title compound.

EXAMPLE 9

Synthesis of 6-(2-dimethylaminoethoxy)-9,10-methylenedioxy-7H-indeno[2,1-c]quinoline-7-on (compound 64)

To a solution prepared with sodium (1.78 g, 77.4 mmol) and 2-dimethylaminoethanol (80 ml, 796 mmol) was added 6-chloro-9,10-methylenedioxy-7H-indeno[2,1-c]quinoline-7-on (8 g, 25.8 mmol) obtained in reference example 2, and the mixture was stirred with heat at 60° C. for 24 hours. The reaction mixture was poured into ice water and extracted with chloroform. The chloroform layer was dried over magnesium sulfate and evaporated. The residue was purified by silica gel column chromatography (eluent; chloroform:methanol=10:1(v/v)) and crystallized from ethyl acetate to give 6.37 g (yield: 68.1%) of title compound. The physicochemical properties thereof are shown in table 2.

The compound obtained was dissolved in chloroform to filter off undissolved substances. The filtrate was acidified with 4N-hydrochloride in ethyl acetate to collect a crystal precipitated. The crystal obtained was dried under reduced pressure to give a salt of compound 64 (compound 64-a) quantitatively. Physicochemical properties thereof were shown in table 1.

EXAMPLES 10–74

The compounds 6–58 and 62–63 shown in table 1, compounds 65–72 shown in table 2, compound 73 shown in table 3 and compound 74 shown in table 4 were synthesized according to the same procedures as shown in examples 1–9 from corresponding starting materials.

In addition, compounds 9-a, 23-a, 26-a, 28-a, 31-a, 41-a, 47-a, 49-a, 50-a, 66-a and 73-a were prepared as hydrochloride in the same procedure as examples 1, 3 and 9 for producing hydrochloride of compounds 1-a, 3-a and 64-a.

EXAMPLE 75

Synthesis of 6-(1-(4-methylpiperazinyl))-7H-indeno[2,1-c]isoquinoline-7-on (compound 75)

A mixture of 5-chloro-7H-indeno[2,1-c]isoquinoline-7-on obtained in reference example 17 (1.0 g, 3.7 mmol), N-methylpiperazine (2 ml, 18 mmol) and N,N-dimethylformamide (10 ml) was stirred at 100° C. for 4 hours. To the reaction mixture was added water and the mixture was extracted with ethyl acetate. The ethyl acetate layer was dried over magnesium sulfate and evaporated. The residue was purified by silica gel column chromatography (eluent; chloroform:methanol=100:1(v/v)) and crystallized from ethanol to give 400 mg (yield: 32.3%) of title compound. The physicochemical properties thereof are shown in table 5.

EXAMPLES 76–80

The compounds 76–80 shown in table 5 were synthesized according to the same procedures as shown in examples 75 from corresponding starting materials.

The results of test on antitumor effects of compounds of the invention are shown below to make clear usefulness of the compounds of the invention.

TABLE 1

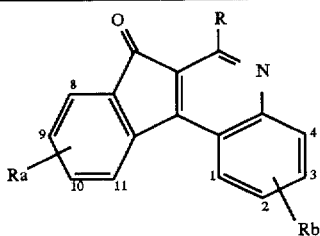

Compound 1
R=—NHCH$_2$CH$_2$N(CH$_3$)$_2$
Ra=H
Rb=3-OCH$_3$
Yield: 55.3%
m.p.: 165°–168° C.
$^1$H-NMR(CDCl$_3$) δ: 8.12(1H, d, J=9 Hz), 7.97(1H, d, J=8 Hz), 7.65(1H, d, J=7 Hz), 7.52(1H, d-d, J=8,8 Hz), 7.41(1H, d-d, J=8,7 Hz), 7.34(1H, brt), 7.07(1H, d, J=2 Hz), 6.93(1H, d-d, J=9,2 Hz), 3.95(3H, s), 3.76(2H, d-t, J=6,6 Hz), 2.63(2H, t, J=6 Hz), 2.34(6H, s).
IR(KBr)cm$^{-1}$: 3370, 2940, 2810, 2770, 1685, 1617, 1602, 1585, 1569, 1530, 1475, 1461, 1419, 1267, 1255, 1235, 1195, 1158, 864, 750.

Compound 1-a
R=—NHCH$_2$CH$_2$N(CH$_3$)$_2$.2HCl.3/5H$_2$O
Ra=H
Rb=3-OCH$_3$
m.p.: 208°–210° C.
IR(KBr)cm$^{-1}$: 3310, 1701, 1649, 1623, 1600, 1504, 1470, 1434, 1421, 1391, 1300, 1282, 1173.

Compound 2
R=—NHCH$_2$CH$_2$N(CH$_3$)$_2$.2HCl
Ra=H
Rb=3-F
Yield: 34.3%
m.p.: 230°–231° C.
$^1$H-NMR(DMSO-d$_6$) δ: 10.05(1H, brs), 8.62(1H, m), 8.37(1H, d, J=8 Hz), 7.79–7.31(6H, m), 3.99(2H, m), 3.41(2H, m), 2.87(6H, d, J=4 Hz).
IR(KBr)cm$^{-1}$: 700, 1706, 1658, 1617, 1473, 1460, 1415, 1392, 1261, 757, 720.

Compound 3
R=—NHCH$_2$CH$_2$N(CH$_3$)$_2$
Ra=H
Rb=3-OH
Yield: 73.0%
m.p.: 215°–217° C.
$^1$H-NMR(Acetone-d$_6$) δ: 8.33(1H, d, J=9Hz), 8.24(1H, d, J=7 Hz), 7.68–7.50(3H, m), 7.38(1H, brs), 7.18(1H, d, J=2 Hz), 7.00(1H, d-d, J=9,2 Hz), 3.80(2H, d-t, J=6,6 Hz), 2.78(2H, t, J=6 Hz), 2.47(6H, s).
IR(KBr)cm$^{-1}$: 3360, 1682, 1615, 1592, 1547, 1460, 1424, 1396, 1384, 1198.

Compound 3-a
R=—NHCH$_2$CH$_2$N(CH$_3$)$_2$.2HCl.3/4H$_2$O
Ra=H
Rb=3-OH
m.p.: 228° C. (decomp.)
IR(KBr)cm$^{-1}$: 3410, 2970, 1700, 1642, 1621, 1469, 1430, 1400, 1313, 1208.

Compound 4
R=—NHCH$_2$CH$_2$N(CH$_3$)$_2$
Ra=H
Rb=3-OCOC(CH$_3$)$_3$
Yield: 80.0%
m.p.: 184°–186° C.
$^1$H-NMR(CDCl$_3$) δ: 8.22(1H, d, J=9 Hz), 7.99(1H, d, J=8 Hz), 7.67(1H, d, J=8 Hz), 7.55(1H, d-d-d, J=8,8,1 Hz), 7.45–7.39(2H, m), 7.31(1H, brt), 7.03(1H, d-d, J=9,2 Hz), 3.75(2H, d-t, J=6,6 Hz), 2.63(2H, t, J=6 Hz), 2.34(6H, s), 1.40(9H, s).
IR(KBr)cm$^{-1}$: 3490, 2980, 1747, 1695, 1624, 1589, 1532, 1461, 1419, 1153, 1138, 1123, 1109, 753.

Compound 5
R=—NHCH$_2$CH$_2$N(CH$_3$)$_2$
Ra=H
Rb=3-OH, 4-NO$_2$
Yield: 52.9%
m.p.: 170°–173° C. (decomp.)
$^1$H-NMR(DMSO-d$_6$) δ: 8.18(1H, d, J=8 Hz), 8.08(1H, d, J=9 Hz), 7.63–7.47(3H, m), 6.62(1H, d, J=9 Hz), 3.76(2H, m), 3.27(1H, brt), 2.79(6H, s).
IR(KBr)cm$^{-1}$: 3380, 1608, 1597, 1581, 1511, 1504, 1461, 1427, 1385.

Compound 6
R=—NHCH$_2$CH$_2$N(C$_2$H$_5$)$_2$
Ra=H
Rb=3-OCH$_3$
Yield: 51.2%
m.p.: 90°–93° C.
$^1$H-NMR(CDCl$_3$) δ: 8.12(1H, d, J=9 Hz), 7.97(1H, d, J=7 Hz), 7.66(1H, d, J=6 Hz), 7.60–7.30(3H, m), 7.06(1H, d, J=2 Hz), 6.92(1H, d-d, J=9,2 Hz), 3.95(3H, s), 3.73(2H, d-t, J=6,5 Hz), 2.77(2H, t, J=6 Hz), 2.65(4H, q, J=7 Hz), 1.12(6H, t, J=7 Hz).
IR(KBr)cm$^{-1}$: 3380, 2970, 2800, 1688, 1619, 1587, 1535, 1196, 755.

Compound 7
R=—NHCH$_2$CH$_2$N(C$_2$H$_5$)$_2$.2HCl
Ra=H
Rb=3-OH
Yield: 42.3%
m.p.: 224° C. (decomp.)
$^1$H-NMR(DMSO-d$_6$) δ: 8.49(1H, d, J=9 Hz), 8.36(1H, d, J=7 Hz), 7.80–7.60(3H, m), 7.40(1H, brs), 7.13(1H, d-d, J=9,2 Hz), 4.08(5H, m), 3.42(2H, t, J=6 Hz), 3.27(4H, q, J=7 Hz), 1.28(6H, t, J=7 Hz ).
IR(KBr)cm$^{-1}$: 3400, 2970, 2670, 1694, 1640, 1614, 1432, 1316, 750.

Compound 8

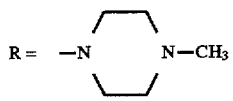

Ra=H
Rb=3-OCH$_3$
Yield: 90.9%
m.p.: 141°–144° C.
$^1$H-NMR(CDCl$_3$) δ: 8.20(1H, d, J=9 Hz), 7.98(1H,m), 7.65(1H,m), 7.55–7.35(2H, m), 7.08(1H, m), 7.00(1H, m), 3.95(3H, s), 3.71(4H, brs), 2.69(4H, brs), 2.40(3H, s).
IR(KBr)cm$^{-1}$: 2950, 2850, 2790, 1696, 1617, 1568, 1418, 1196.

Compound 9

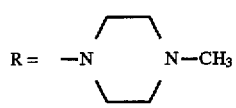

Ra=H
Rb=3-OH
Yield: 86.1%
m.p.: 227°–229° C. (decomp.)
¹H-NMR(DMSO-d₆) δ: 8.43(1H, d, J=9 Hz), 8.31(1H, d, J=8 Hz), 7.67–7.50(3H, m), 7.03(1H, d-d, J=9,2 Hz), 6.95(1H, d, J=2 Hz), 3.55(4H, brs), 2.51–2.50(4H, m), 2.25(3H, s).
IR(KBr)cm⁻¹: 2840, 2800, 1698, 1615, 1567, 1556, 1461, 1451, 1444, 1428, 1301, 1255, 1244, 1199, 1144, 921.

Compound 9-a

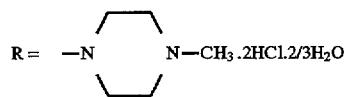

Ra=H
Rb=3-OH
m.p.: 273° C. (decomp.)
IR(KBr)cm⁻¹: 3400, 3020, 2970, 1707, 1626, 1600, 1585, 1483, 1443, 1427, 1416, 1368, 1336, 1252.

Compound 10
R=—NHCH₂CH₂CH₂N(C₂H₅)₂
Ra=H
Rb=3-OH
Yield: 63.4%
m.p.: 152°–155° C.
¹H-NMR(CDCl₃) δ: 7.72(1H, d, J=9 Hz), 7.53–7.19(6H, m), 6.77(1H, d-d, J=9,2 Hz), 3.53(2H, m), 2.57(6H, m), 1.85(2H, m), 1.00(6H, t, J=7 Hz).
IR(KBr)cm⁻¹: 3390, 2980, 1706, 1644, 1621, 1468, 1313.

Compound 11
R=—NHCH₂CH₂CH(CH₃)₂.HCl
Ra=H
Rb=3-OH
Yield: 27.8%
m.p.: 220°–223° C.
¹H-NMR(DMSO-d₆) δ: 8.15(1H, d, J=9 Hz), 8.00(1H, d, J=7 Hz), 7.58–7.44(3H, m), 7.28(1H, d, J=2 Hz), 6.99(1H, d-d, J=9,2 Hz), 3.50(2H, m), 1.73(1H, m), 1.57(2H, m), 1.00(6H, d, J=7 Hz).
IR(KBr)cm⁻¹: 3320, 2950, 2870, 1694, 1647, 1621, 1470, 1320, 1204.

Compound 12

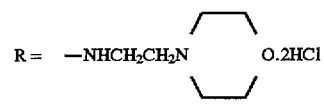

Ra=H
Rb=3-OH
Yield: 33.8%
m.p.: 172° C. (decomp.)
¹H-NMR(DMSO-d₆) δ: 8.54(1H, d, J=9 Hz), 8.40(1H, d, J=8 Hz), 7.78–7.61(4H, m), 7.17(1H, d, J=9 Hz), 4.20–3.43(10H, m), 2.53(2H, brs).
IR(KBr)cm⁻¹: 3480, 2920, 2660, 1700, 1642, 1620.

Compound 13
R=—NHCH₂CH₂CH₂N(CH₃)₂
Ra=H
Rb=3-OCH₃
Yield: 40.9%
m.p.: 123°–126° C.
¹H-NMR(CDCl₃) δ: 8.06(1H, d, J=9 Hz), 7.92(1H, d, J=8 Hz), 7.63(1H, d, J=7 Hz), 7.52–7.35(2H, m), 7.25(1H, brs), 7.02(1H, d, J=2 Hz), 6.88(1H, d-d, J=9,2 Hz), 3.94(3H, s), 3.72(2H, d-t, J=6,7 Hz), 2.46(2H, t, J=7 Hz), 2.30(6H, s), 1.95–1.85(2H, m).
IR(KBr)cm⁻¹: 2920, 2760, 1687, 1620, 1587, 1418, 1196.

Compound 14
R=—N(CH₃)CH₂CH₂N(CH₃)₂
Ra=H
Rb=3-OH
Yield: 24.3%
m.p.: 150° C. (decomp.)
¹H-NMR(CDCl₃) δ: 7.93(1H, d, J=9 Hz), 7.84(1H, d, J=7 Hz), 7.66–7.63(1H, m), 7.46–7.37(2H, m), 6.84(1H, d-d, J=9,2 Hz), 6.72(1H, brs), 3.78(2H, t, J=6 Hz), 3.25(3H, s), 2.86(2H, t, J=6 Hz), 2.55(6H, s).
IR(KBr)cm⁻¹: 3400, 1691, 1611, 1511.

Compound 15

Ra=H
Rb=3-OH
Yield: 62.3%
m.p.: 218° C. (decomp.)
¹H-NMR(DMSO-d₆) δ: 7.64(1H, d, J=9 Hz), 7.48–7.33(4H, m), 6.72(1H, brd, J=9 Hz), 6.59(1H, s), 3.71(2H, t, J=6 Hz), 3.60(2H, m), 3.34(2H, t, J=6 Hz), 3.05(2H, m), 1.96–1.50(6H, m).
IR(KBr)cm⁻¹: 3290, 2950, 2660, 1699, 1642, 1620, 1472, 1431, 1308, 1206.

Compound 16

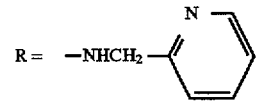

Ra=H
Rb=3-OH
Yield: 31.2%
m.p.: 255°–259° C.
¹H-NMR(DMSO-d₆) δ: 10.54(1H, brs), 8.59(1H, d, J=5 Hz), 8.36–8.27(2H, m), 7.96(1H, t, J=5 Hz), 7.77(1H, d-d-d, J=8,8,2 Hz), 7.68–7.63(2H, m), 7.54(1H, d-d, J=8,7 Hz), 7.44(1H, d, J=8 Hz), 7.32–7.27(1H, m), 6.94(1H, d-d, J=9,3 Hz), 6.87(1H, d, J=2 Hz), 4.89(2H, d, J=5Hz).
IR(KBr)cm⁻¹: 2710, 1706, 1622, 1606, 1431, 1315, 730.

Compound 17
R=—NHCH(CH₃)CH₂CH₂CH₂N(C₂H₅)₂
Ra=H
Rb=3-OCH₃
Yield: 50.0%
m.p.: 105°–107° C.
¹H-NMR(CDCl₃) δ: 8.10(1H, d, J=9 Hz), 7.96(1H, d, J=7 Hz), 7.64(1H, d-d, J=7,1 Hz), 7.55–7.35(2H, m), 7.03(1H, d, J=2.5 Hz), 6.91(1H, d-d, J=9,2.5 Hz), 6.87(1H, s), 4.52(1H, m), 3.95(3H, s), 2.58–2.50(6H, m), 1.63(4H, m), 1.33(3H, d, J=7 Hz), 1.01(6H, t, J=7 Hz).
IR(KBr)cm⁻¹: 3370, 2990, 1683, 1618, 1600, 1421, 1196.

Compound 18
R=—NHCH(CH$_3$)CH$_2$CH$_2$CH$_2$N(C$_2$H$_5$)$_2$
Ra=H
Rb=3-OH
Yield: 27.6%
m.p.: 96°–100° C.
$^1$H-NMR(CDCl$_3$) δ: 7.68(1H, d, J=9 Hz), 7.65–7.25(4H, m), 6.93(1H, s), 6.83(1H, d, J=8 Hz), 6.70(1H, d-d, J=9,2 Hz), 4.37(1H, m), 2.68–2.59(6H, m), 1.63(4H, m), 1.22(3H, d, J=6 Hz), 1.02(6H, t, J=7 Hz).
IR(KBr)cm$^{-1}$: 3350, 2960, 2920, 1682, 1578, 1422, 1272, 1190, 927, 750, 540.
Compound 19
R=—NHCH$_2$CH$_2$N(C$_2$H$_5$)$_2$
Ra=9-OH
Rb=H
Yield: 83.1%
m.p.: 98°–102° C.
$^1$H-NMR(CDCl$_3$) δ: 7.67–7.57(2H, m), 7.45(1H, d, J=8 Hz), 7.06(1H, m), 6.91(1H, t, J=6 Hz), 6.81(1H, d, J=2 Hz), 6.65(1H, d, J=8 Hz), 6.06(1H, d-d, J=8,2 Hz), 3.89(2H, d-t, J=6,5 Hz), 2.98(2H, t, J=5 Hz), 2.87(4H, q, J=7 Hz), 1.15(6H, t, J=7 Hz).
IR(KBr)cm$^{-1}$: 3400, 2980, 2810, 1689, 1588, 1530, 1274, 802.
Compound 20
R=—OCH$_2$CH$_2$N(CH$_3$)$_2$
Ra=H Rb = 3-OCH$_2$— 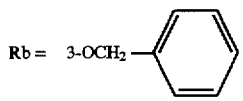

Yield: 70.1%
m.p.: 95°–100° C.
$^1$H-NMR(CDCl$_3$) δ: 8.29(1H, d, J=9 Hz), 8.02(1H, d, J=7 Hz), 7.71(1H, d, J=7 Hz), 7.58–7.17(9H, m), 5.22(2H, s), 4.73(2H, t, J=6 Hz), 2.88(2H, t, J=6 Hz), 2.43(6H, s).
IR(KBr)cm$^{-1}$: 2950, 1705, 1616, 1574, 1435, 1149.
Compound 21
R=—NHCH$_2$CH$_2$N(CH$_3$)$_2$
Ra=H
Rb=3-Cl
Yield: 59.7%
m.p.: 154°–158° C.
$^1$H-NMR(CDCl$_3$) δ: 8.08(1H, d, J=9 Hz), 7.91(1H, d, J=8 Hz), 7.68(1H, d, J=2 Hz), 7.64(1H, d-d, J=7,1 Hz), 7.55–7.39(2H, m), 7.31(1H, brs), 7.18(1H, d-d, J=9,2 Hz), 3.73(2H, d-t, J=6,6 Hz), 2.61(2H, t, J=6 Hz), 2.34(6H, s).
IR(KBr)cm$^{-1}$: 3380, 2780, 1698, 1587, 1525, 1070, 751.
Compound 22
R=—OCH$_2$CH$_2$N(CH$_3$)$_2$
Ra=H
Rb=3-OCH$_3$
Yield: 46.7%
m.p.: 154°–158° C.
$^1$H-NMR(CDCl$_3$) δ: 8.27(1H, d, J=9 Hz), 8.02(1H, d, J=7 Hz), 7.71(1H, d-d, J=7,1 Hz), 7.52–7.35(2H, m), 7.19(1H, d, J=2.5 Hz), 7.12(1H, d-d, J=9,2.5 Hz), 4.73(2H, t, J=6 Hz), 2.89(2H, t, J=6 Hz), 2.43(6H, s).
IR(KBr)cm$^{-1}$: 2800, 2760, 1708, 1617, 1576, 1195.
Compound 23
R=—NHCH$_2$CH$_2$N(CH$_3$)$_2$
Ra=9-Cl
Rb=3-OH
Yield: 37.4%
m.p.: 140°–144° C.
$^1$H-NMR(DMSO-d$_6$) δ: 8.27(2H, d, J=9 Hz), 7.67(1H, d-d, J=8,2 Hz), 7.59(1H, d, J=2 Hz), 7.24(1H, brs), 6.92(1H, d-d, J=9,3 Hz), 6.87(1H, d, J=3Hz), 3.65–3.59(2H, m), 2.55–2.50(2H, m), 2.25(6H, s).
IR(KBr)cm$^{-1}$: 3400, 2950, 2800, 1683, 1593, 1531, 1192.
Compound 23-a
R=—NHCH$_2$CH$_2$N(CH$_3$)$_2$.2HCl
Ra=9-Cl
Rb=3-OH
m.p.: 197°–201° C.
IR(KBr)cm$^{-1}$: 3390, 2970, 1704, 1642, 1621, 1470, 1446, 1424, 1315.
Compound 24
R=—NHCH$_2$CH$_2$N(CH$_3$)$_2$
Ra=9-Cl
Rb=3-OCH$_3$
Yield: 19.2%
m.p.: 88°–92° C.
$^1$H-NMR(CDCl$_3$) δ: 8.03(1H, d, J=9 Hz), 7.87(1H, d, J=8 Hz), 7.58(1H, d, J=2 Hz), 7.46(1H, d-d, J=8,2 Hz), 7.04(1H, d, J=2.5 Hz), 6.93(1H, d-d, J=9,2.5 Hz), 3.95(3H, s), 3.79 (2H, d-t, J=6,6 Hz), 2.75(2H, t, J=6 Hz), 2.42(6H, s).
IR(KBr)cm$^{-1}$: 3400, 2950, 2800, 1688, 1618, 1594, 1427, 1200.
Compound 25
R=—NHCH$_2$CH$_2$N(CH$_3$)$_2$
Ra=9-OH, 10-OH
Rb=H
Yield: 51.7%
m.p.: 191°–195° C.
$^1$H-NMR(DMSO-d$_6$) δ: 8.16(1H, d, J=9 Hz), 7.67–7.27 (4H, m), 7.17(1H, brt), 7.00(1H, s), 3.64(2H, m), 2.61(2H, t, J=6 Hz), 2.31(6H, s).
IR(KBr)cm$^{-1}$: 2950, 1676, 1592, 1530, 1372, 1050.
Compound 26

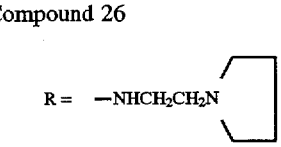

Ra=H
Rb=3-OH
Yield: 79.3%
m.p.: 130°–134° C.
$^1$H-NMR(CDCl$_3$) δ: 7.60(1H, d, J=9 Hz), 7.12–7.49(6H, m), 6.68(1H, d, J=9 Hz), 3.66(2H, m), 2.86(2H, m), 2.70 (4H, m), 1.85(4H, m).
IR(KBr)cm$^{-1}$: 3400, 2950, 2800, 1681, 1580, 1460, 1423, 1191, 1168, 1154, 928, 750, 580.
Compound 26-a

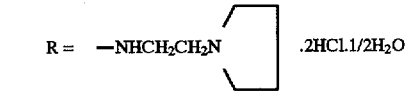

Ra=H
Rb=3-OH
m.p.: 242° C. (decomp.)
IR(KBr)cm$^{-1}$: 3290, 2980, 1700, 1641, 1621, 1610, 1500, 1470, 1435, 1405, 1308, 1207.

Compound 27

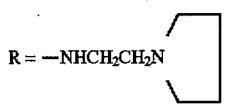

Ra=H
Rb=3-OCH$_3$
Yield: 33.4%
m.p.: 128°–132° C.
$^1$H-NMR(CDCl$_3$) δ: 8.09(1H, d, J=9 Hz), 7.95(1H, d, J=7 Hz), 7.64(1H, d, J=7 Hz), 7.45(2H, m), 7.31(1H, brt), 7.05(1H, d, J=2.5 Hz), 6.91(1H, d-d, J=9,2.5 Hz), 3.95(3H, s), 3.81(2H, d-t, J=7,5 Hz), 2.82(2H, t, J=7 Hz), 2.64(4H, m), 1.83(4H, m).
IR(KBr)cm$^{-1}$: 3380, 2960, 2780, 1689, 1619, 1601, 1420, 1257, 1197.

Compound 28
R=—NHCH$_2$CH$_2$N(CH$_3$)$_2$
Ra=H
Rb=H
Yield: 41.9%
m.p.: 95°–99° C.
$^1$H-NMR(CDCl$_3$) δ: 8.22(1H, d, J=8 Hz), 8.02(1H, d, J=8 Hz), 7.72–7.24(8H, m), 3.78(2H, d-t, J=6,6 Hz), 2.65(2H, t, J=6 Hz), 2.36(6H, s).
IR(KBr)cm$^{-1}$: 3400, 2780, 1687, 1622, 1586, 1573, 1534, 1343, 757, 730, 613, 466, 442, 418.

Compound 28-a
R=—NHCH$_2$CH$_2$N(CH$_3$)$_2$.2HCl.1/5H$_2$O
Ra=H
Rb=H
m.p.: 236° C. (decomp.)

Compound 29
R=—NHCH$_2$CH$_2$N(CH$_3$)$_2$
Ra=H
Rb=2-Cl
Yield: 46.9%
m.p.: 128°–131° C.
$^1$H-NMR(CDCl$_3$) δ: 8.04(1H, d, J=2 Hz), 7.87(1H, d, J=7 Hz), 7.63–7.23(6H, m), 3.72(2H, d-t, J=6,6 Hz), 2.62(2H, t, J=6 Hz), 2.35(6H, s).
IR(KBr)cm$^{-1}$: 2770, 1693, 1631, 1614, 1589, 1568, 1558, 1527, 1462, 1441, 1410, 1272, 822, 752.

Compound 30
R=—NHCH$_2$CH$_2$N(CH$_3$)$_2$
Ra=H
Rb=2-OCH$_3$
Yield: 17.4%
m.p.: 152°–156° C.
$^1$H-NMR(CDCl$_3$) δ: 7.94(1H, d, J=7 Hz), 7.67(1H, d, J=7 Hz), 7.65(1H, d, J=9 Hz), 7.55(1H, d-d-d, J=7,7,1 Hz), 7.47(1H, d, J=2.5 Hz), 7.41(1H, d-d, J=7,7 Hz), 7.34(1H, d-d, J=9,2.5 Hz), 7.16(1H, brs), 3.97(3H, s), 3.76(2H, d-t, J=6,6 Hz), 2.64(2H, t, J=6 Hz), 2.35(6H, s).
IR(KBr)cm$^{-1}$: 3370, 1679, 1588, 1567, 1531, 1476, 1463, 1450, 1425, 1318, 1309, 1280, 1233, 1215, 1202, 1114, 1057, 1043, 1030, 974, 819, 756.

Compound 31
R=—NHCH$_2$CH$_2$N(CH$_3$)$_2$
Ra=H
Rb=2-OH
Yield: 78.2%
m.p.: 195°–199° C.
$^1$H-NMR(CDCl$_3$) δ: 7.60(1H, d, J=8 Hz), 7.46(1H, d, J=7 Hz), 7.35(1H, d-d-d, J=8,8,1 Hz), 7.17(1H, d-d, J=8,7 Hz), 6.92(1H, d, J=3 Hz), 6.87–6.76(3H, m), 3.91(2H, d-t, J=6,6 Hz), 2.91(2H, t, J=6 Hz), 2.55(6H, s).
IR(KBr)cm$^{-1}$: 3390, 1689, 1683, 1593, 1573, 1547, 1537, 1465, 1428, 1389, 1373, 1324, 1276, 1222, 1203, 821.

Compound 31-a
R=—NHCH$_2$CH$_2$N(CH$_3$)$_2$.2HCl.2/3H$_2$O
Ra=H
Rb=2-OH
m.p.: 262° C. (decomp.)
IR(KBr)cm$^{-1}$: 2950, 2690, 1704, 1655, 1618, 1476, 1444, 1397, 1265, 1233, 752.

Compound 32
R=—N(CH$_3$)$_2$
Ra=H
Rb=2-NO$_2$
Yield: 73.4%
m.p.: 287°–288° C. (decomp.)
$^1$H-NMR(CDCl$_3$) δ: 9.30(1H, d, J=2 Hz), 8.38(1H, d-d, J=10,2 Hz), 8.15(1H, d, J=8 Hz), 7.74(1H, d, J=10 Hz), 7.70–7.49(3H, m), 3.33(6H, s).
IR(KBr)cm$^{-1}$: 1703, 1617, 1580, 1558, 1489, 1341, 891, 840, 758, 719, 433.

Compound 33
R=—NHCH$_2$CH$_2$N(CH$_3$)$_2$
Ra=H
Rb=2-NH$_2$
Yield: 16.9%
m.p.: 210°–214° C.
$^1$H-NMR(CDCl$_3$) δ: 7.95(1H, d, J=8 Hz), 7.65(1H, d, J=7 Hz), 7.58(1H, d, J=9 Hz), 7.52(1H, d-d, J=8,8 Hz), 7.41–7.35(2H, m), 7.14(1H, d-d, J=9,3 Hz), 7.10(1H, brs), 3.83(2H, brs), 3.74(2H, m), 2.62(2H, t, J=6 Hz), 2.34(6H, s).
IR(KBr)cm$^{-1}$: 3370, 2360, 1677, 1631, 1597, 1582, 1565, 1518, 1474, 1459, 1426, 1311, 1257, 1233, 896, 826, 758.

Compound 34
R=—NHCH$_2$CH$_2$N(CH$_3$)$_2$
Ra=H
Rb=3-CH$_3$
Yield: 55.7%
m.p.: 144°–148° C.
$^1$H-NMR(CDCl$_3$) δ: 8.11(1H, d, J=9 Hz), 8.00(1H, d, J=8 Hz), 7.65(1H, d, J=8 Hz), 7.56–7.50(2H, m), 7.41(1H, m), 7.11(1H, d-d, J=9,2 Hz), 3.77(2H, m), 2.64(2H, t, J=6 Hz), 2.49(3H, s), 2.36(6H, s).
IR(KBr)cm$^{-1}$: 3390, 1688, 1625, 1600, 1584, 1564, 1524, 1461, 1416, 1378, 1270, 935, 752.

Compound 35
R=—N(CH$_3$)CH$_2$CH$_2$N(CH$_3$)$_2$
Ra=H
Rb=3-OCH$_3$
Yield: 79.8%
m.p.: 90°–94° C.
$^1$H-NMR(CDCl$_3$) δ: 8.22(1H, d, J=9 Hz), 8.02(1H, d, J=7 Hz), 7.67(1H, d, J=8 Hz), 7.53(1H, d-d, J=8,8 Hz), 7.42(1H, d-d, J=8,7 Hz), 7.05(1H, d, J=3 Hz), 6.97(1H, d-d, J=9,3 Hz), 3.96(3H, s), 3.85(2H, t, J=7 Hz), 3.26(3H, s), 2.71(2H, t, J=7 Hz), 2.32(6H, s).
IR(KBr)cm$^{-1}$: 2940, 2820, 2770, 1693, 1620, 1604, 1573, 1549, 1529, 1462, 1446, 1418, 1305, 1263, 1238, 1187, 1138, 751.

Compound 36
R=—N(CH$_3$)$_2$
Ra=H
Rb=3-OH
Yield: 41.0%
m.p.: 258–260° C. (decomp.)
$^1$H-NMR(CDCl$_3$) δ: 8.21(1H, d, J=9 Hz), 8.02(1H, d, J=7 Hz), 7.66(1H, d, J=7 Hz), 7.53(1H, m), 7.42(1H, d-d, J=8,7 Hz), 7.11(1H, d, J=2 Hz), 6.99(1H, d-d, J=9,2 Hz), 3.22(6H, s).

IR(KBr)cm$^{-1}$: 2370, 1700, 1621, 1604, 1573, 1557, 1531, 1461, 1427, 1259, 922.

Compound 37
R=—NHCH$_3$.HCl
Ra=H
Rb=3-OH
Yield: 88.2%
m.p.: >290° C.
$^1$H-NMR(DMSO-d$_6$) δ: 11.92(1H, brs), 8.70(1H, brs), 8.56(1H, d, J=9 Hz), 8.42(1H, d, J=8 Hz), 7.76–7.63(4H, m), 7.14(1H, d-d, J=9,2 Hz), 3.25(3H, d, J=5 Hz).
$^1$H-NMR(DMSO-d$_6$+D$_2$O) δ: 8.55(1H, d, J=9 Hz), 8.39(1H, d, J=7 Hz), 7.77–7.64(3H, m), 7.49(1H, d, J=2 Hz), 7.14(1H, d-d, J=9,2 Hz), 3.21(3H, s).
IR(KBr)cm$^{-1}$: 3290, 2920, 1697, 1655, 1621, 1596, 1477, 1462, 1429, 1409, 1317, 1206.

Compound 38
R=—NHCH$_2$CH$_2$OH
Ra=H
Rb=3-OH
Yield: 22.9%
m.p.: 244°–246° C. (decomp.)
$^1$H-NMR(DMSO-d$_6$) δ: 10.54(1H, brs), 8.32(1H, d, J=9 Hz), 8.27(1H, d, J=7 Hz), 7.67–7.49(3H, m), 7.24(1H, brt), 6.92(1H, d-d, J=9,2 Hz), 6.87(1H, d, J=2 Hz), 4.94(1H, brs), 3.63(4H, m).
IR(KBr)cm$^{-1}$: 3380, 1684, 1616, 1596, 1578, 1549, 1459, 1425, 1394, 1270, 1240, 1196, 1056, 929.

Compound 39
R=—NHCH$_2$CH$_2$CH$_2$N(CH$_3$)$_2$
Ra=H
Rb=3-OH
Yield: 70.8%
m.p.: 115°–118° C. (decomp.)
$^1$H-NMR(DMSO-d$_6$) δ: 8.31(1H, d, J=9 Hz), 8.26(1H, d, J=8 Hz), 7.67–7.61(2H, m), 7.52(1H, m), 7.34(1H, brt), 6.92(1H, d, J=9 Hz), 6.88(1H, d, J=2 Hz), 3.60(2H, d-t, J=6,7 Hz), 2.54(2H, t, J=7 Hz), 2.32(6H, s), 1.82(2H, m, J=7 Hz).
IR(KBr)cm$^{-1}$: 2950, 1688, 1614, 1598, 1580, 1585, 1460, 1428, 1392, 1386, 1266, 1191, 1169, 1148, 929.

Compound 40

Ra=H
Rb=3-NHCOCH$_3$
Yield: 58.7%
m.p.: 125°–128° C. (decomp.)
$^1$H-NMR(CDCl$_3$) δ: 8.49(1H, brs), 8.03(1H, d, J=9 Hz), 7.83(1H, d, J=2 Hz), 7.79(1H, d, J=7 Hz), 7.56–7.31(4H, m), 3.64(4H, brs), 2.62(4H, t, J=5 Hz), 2.35(3H, s), 2.26(3H, s).
IR(KBr)cm$^{-1}$: 3300, 2930, 1698, 1619, 1606, 1565, 1532, 1495, 1463, 1448, 1430, 1371, 1266, 1248, 756.

Compound 41
R=—NHCH$_2$CH$_2$N(CH$_3$)$_2$
Ra=H
Rb=3-NH$_2$
Yield: 12.6%
m.p.: 155°–156° C. (decomp.)
$^1$H-NMR(CDCl$_3$) δ: 8.05(1H, d, J=9 Hz), 7.94(1H, d, J=7 Hz), 7.63(1H, d, J=7 Hz), 7.49(1H, m), 7.39(1H, m), 6.84(1H, d, J=2 Hz), 6.70(1H, d-d, J=9,2 Hz), 4.22(2H, brs), 3.74(2H, m), 2.61(2H, t, J=6 Hz), 2.34(6H, s).
IR(KBr)cm$^{-1}$: 3360, 3350, 1677, 1615, 1598, 1579, 1529, 1460, 1429.

Compound 41-a
R=—NHCH$_2$CH$_2$N(CH$_3$)$_2$.3HCl.2H$_2$O
Ra=H
Rb=3-NH$_2$
m.p.: 201° C. (decomp.)
IR(KBr)cm$^{-1}$: 3330, 1690, 1623, 1559, 1505, 1473, 1447, 1404.

Compound 42
R=—NHCH$_2$CH$_2$N(CH$_3$)$_2$
Ra=H
Rb=2-OCH$_3$, 3-OCH$_3$
Yield: 47.5%
m.p.: 155°–160° C.
$^1$H-NMR(CDCl$_3$) δ: 7.87(1H, d, J=8 Hz), 7.65(1H, d, J=7 Hz), 7.53(1H, d-d-d, J=8,8,1 Hz), 7.43–7.21(2H, m), 7.40(1H, s), 7.08(1H, s), 4.05(3H, s), 4.04(3H, s), 3.76(2H, d-t, J=6,6 Hz), 2.65(2H, t, J=6 Hz), 2.36(6H, s).
IR(KBr)cm$^{-1}$: 2820, 2770, 1687, 1625, 1587, 1528, 1502, 1477, 1465, 1449, 1429, 1317, 1266, 1243, 1212, 1195, 750.

Compound 43
R=—NHCH$_2$CH$_2$N(CH$_3$)$_2$.2HCl
Ra=H
Rb=2-OH, 3-OH
Yield: 83.3%
m.p.: 275°–277° C. (decomp.)
$^1$H-NMR(DMSO-d$_6$+D$_2$O added) δ: 8.19(1H, d, J=8 Hz), 7.87(1H, s), 7.80–7.73(2H, m), 7.64(1H, d-d, J=8,7 Hz), 7.49(1H, s), 4.06(2H, t, J=6 Hz), 3.43(2H, t, J=6 Hz), 2.90(3H, s).
IR(KBr)cm$^{-1}$: 3380, 1700, 1645, 1623, 1469, 1452, 1319, 1196.

Compound 44
R=—NHCH$_2$CH$_2$N(CH$_3$)$_2$
Ra=8-OCH$_3$
Rb=H
Yield: 63.6%
m.p.: 169°–172° C.
$^1$H-NMR(CDCl$_3$) δ: 8.22(1H, d, J=8 Hz), 7.72–7.23(6H, m), 7.00(1H, d, J=7 Hz), 4.02(3H, s), 3.76(2H, d-d, J=6,6 Hz), 2.62(2H, t, J=6 Hz), 2.33(6H, s).
IR(KBr)cm$^{-1}$: 3370, 2950, 2370, 1689, 1619, 1588, 1564, 1528, 1478, 1461, 1278, 1195, 1066, 811, 800, 765, 725.

Compound 45
R=—NHCH$_2$CH$_2$N(CH$_3$)$_2$
Ra=8-OH
Rb=H
Yield: 38.4%
m.p.: 134°–138° C.
$^1$H-NMR(CDCl$_3$) δ: 8.14(1H, d, J=8 Hz), 7.69(1H, d, J=9 Hz), 7.61(1H, m), 7.50(1H, d, J=7 Hz), 7.38–7.22(2H, m), 7.04(1H, brs), 6.86(1H, d, J=9 Hz), 3.78(2H, m), 2.67(2H, t, J=6 Hz), 2.38(6H, s).
IR(KBr)cm$^{-1}$: 3370, 1673, 1619, 1592, 1533, 1463, 1425, 1415, 1398, 1385, 1357, 1272, 1192, 1139, 1124, 1043, 804, 749, 723.

Compound 46
R=—NHCH$_2$CH$_2$N(CH$_3$)$_2$
Ra=9-OCH$_3$
Rb=H
Yield: 43.4%
m.p.: 105°–109° C.
$^1$H-NMR(CDCl$_3$) δ: 8.16(1H, d, J=8 Hz), 7.91(1H, d, J=8 Hz), 7.70–7.57(2H, m), 7.26–7.22(3H, m), 6.97(1H, d-d, J=8,2 Hz), 3.90(3H, s), 3.77(2H, d-t, J=6,6 Hz), 2.63(2H, t, J=6Hz), 2.35(6H, s).
IR(KBr)cm$^{-1}$: 3380, 2820, 1698, 1613, 1587, 1561, 1529, 1479, 1451, 1432, 1379, 1299, 1272, 1234, 1226, 802, 783, 751.

Compound 47
R=—NHCH$_2$CH$_2$N(CH$_3$)$_2$
Ra=9-OH
Rb=H
Yield: 83.4%
m.p.: 201°–205° C.
$^1$H-NMR(CDCl$_3$) δ: 7.67–7.58(2H, m), 7.41(1H, d, J=8 Hz), 7.07(1H, m), 6.88(1H, brt), 6.77(1H, d, J=2 Hz), 6.52(1H, d, J=8 Hz), 5.92(1H, d-d, J=8,2 Hz), 3.92(2H, m), 2.90(2H, t, J=6 Hz), 2.49(6H, s).
IR(KBr)cm$^{-1}$: 3140, 1695, 1672, 1613, 1597, 1575, 1567, 1535, 1473, 1460, 1444, 1419, 1395, 1361, 1349, 1338, 1293, 1278, 1213, 1206, 818, 799.

Compound 47-a
R=—NHCH$_2$CH$_2$N(CH$_3$)$_2$.2HCl.1/3H$_2$O
Ra=9-OH
Rb=H
m.p.: 237° C. (decomp.)
IR(KBr)cm$^{-1}$: 3220, 2960, 2690, 1707, 1643, 1603, 1587, 1490, 1441, 1391, 1267, 1245, 788.

Compound 48
R=—NHCH$_2$CH$_2$N(CH$_3$)$_2$
Ra=10-OCH$_3$
Rb=H
Yield: 66.1%
m.p.: 180°–184° C.
$^1$H-NMR(CDCl$_3$) δ: 8.17(1H, d, J=9 Hz), 7.71(1H, d, J=9 Hz), 7.63–7.21(6H, m), 6.82(1H, d-d, J=8,2 Hz), 3.95(3H, s), 3.77(2H, d-t, J=6,6 Hz), 2.63(2H, t, J=6 Hz), 2.34(6H, s).
IR(KBr)cm$^{-1}$: 3370, 2780, 1687, 1620, 1610, 1590, 1567, 1529, 1453, 1380, 1288, 1278, 1226, 1087.

Compound 49
R=—NHCH$_2$CH$_2$N(CH$_3$)$_2$
Ra=10-OH
Rb=H
Yield: 71.6%
m.p.: 184°–188° C.
$^1$H-NMR(DMSO-d$_6$) δ: 8.28(1H, d, J=9 Hz), 7.71–7.59(3H, m), 7.50(1H, d, J=8 Hz), 7.37–7.27(2H, m), 6.82(1H, d, J=8 Hz), 3.67(2H, m), 2.60(2H, t, J=6 Hz), 2.30(6H, s).
IR(KBr)cm$^{-1}$: 3380, 1680, 1620, 1593, 1537, 1466, 1454, 1410, 1379, 1307, 1285, 1252, 1071, 841, 740, 725.

Compound 49-a
R=—NHCH$_2$CH$_2$N(CH$_3$)$_2$.2HCl.4/5H$_2$O
Ra=10-OH
Rb=H
m.p.: 243° C. (decomp.)
IR(KBr)cm$^{-1}$: 2970, 2700, 1695, 1653, 1617, 1595, 1466, 1451, 1391, 1278, 1260.

Compound 50
R=—NHCH$_2$CH$_2$N(CH$_3$)$_2$
Ra=9-OH
Rb=3-OH
Yield: 70.2%
m.p.: 203°–207° C. (decomp.)
$^1$H-NMR(CD$_3$OD) δ: 8.00(1H, d, J=9 Hz), 7.77(1H, d, J=8 Hz), 6.95(1H, d, J=3 Hz), 6.85–6.78(2H, m), 6.72(1H, d, J=2 Hz), 3.71(2H, t, J=6 Hz), 2.83(2H, t, J=6 Hz), 2.53(6H, s).
IR(KBr)cm$^{-1}$: 3370, 1683, 1588, 1542, 1533, 1529, 1456, 1422, 1346, 1324, 1269, 1196, 1141, 578.

Compound 50-a
R=—NHCH$_2$CH$_2$N(CH$_3$)$_2$.2HCl
Ra=9-OH
Rb=3-OH
m.p.: 207° C. (decomp.)
IR(KBr)cm$^{-1}$: 3360, 1680, 1587, 1533, 1422, 1347, 1269, 1195, 1140, 1119, 579.

Compound 51
R=—OCH$_2$CH$_3$
Ra=H
Rb=H
Yield: 49.3%
m.p.: 179°–183° C.
$^1$H-NMR(CDCl$_3$) δ: 8.40(1H, d, J=9 Hz), 8.09(1H, d, J=8 Hz), 7.86(1H, d, J=9 Hz), 7.77–7.71(2H, m), 7.58(1H, d-d-d, J=8,8,1 Hz), 7.52–7.43(2H, m), 4.70(2H, q, J=7 Hz), 1.54(3H, t, J=7 Hz).
IR(KBr)cm$^{-1}$: 2970, 1713, 1571, 1511, 1426, 1329, 1312, 1275, 1157, 1037, 929, 764.

Compound 52

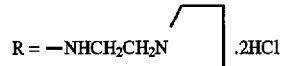

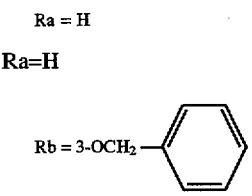

Ra=H

Yield: 61.6%
m.p.: 162° C. (decomp.)
$^1$H-NMR(DMSO-d$_6$) δ: 10.00(1H, brs), 8.50(1H, d, J=9.5 Hz), 8.38(1H, d, J=8 Hz), 7.73–7.37(9H, m), 7.18(1H, d-d, J=9,2 Hz), 5.31(2H, s), 4.11–3.17(8H, m), 1.94(4H, brs).
IR(KBr)cm$^{-1}$: 3400, 2680, 1705, 1643, 1620, 1433, 1392, 1289, 1266, 1213, 755.

Compound 53
R=—NHCH$_2$CH$_2$N(CH$_3$)$_2$.2HCl
Ra=H

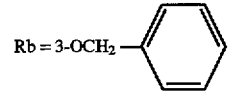

Yield: 70.2%
m.p.: 139° C. (decomp.)
$^1$H-NMR(DMSO-d$_6$) δ: 9.80(1H, brs), 8.50(1H, d, J=9 Hz), 8.38(1H, d, J=8 Hz), 7.73–7.38(9H, m), 7.19(1H, d-d, J=8.5, 1.5 Hz), 5.31(2H, s), 4.00(2H, m), 3.42(2H, m), 2.88(6H, d, J=4 Hz).
IR(KBr)cm$^{-1}$: 3400, 2690, 1704, 1643, 1620, 1469, 1433, 1393, 1288, 1268, 1212, 1174, 754.

Compound 54

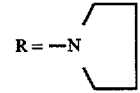

Ra=H
Rb=3-OCH$_3$
Yield: 75.2%
m.p.: 154°–156° C.
$^1$H-NMR(CDCl$_3$) δ: 8.21(1H, d, J=9 Hz), 8.02(1H, d, J=7 Hz), 7.66(1H, d, J=7 Hz), 7.52(1H, d-d-d, J=8,8,1 Hz), 7.42(1H, d-d, J=8,7 Hz), 7.04(1H, d, J=3 Hz), 6.92(1H, d-d, J=9,3 Hz), 3.95(3H, s), 3.81(4H, m), 1.98(4H, m).
IR(KBr)cm$^{-1}$: 2960, 1697, 1621, 1568, 1547, 1505, 1460, 1444, 1415, 1203, 1195, 917, 751.

Compound 55
R=—NHCH$_2$CH$_2$NHCH$_2$CH$_2$OH.2HCl
Ra=H
Rb=3-OH
Yield: 93.7%
m.p.: 230° C. (decomp.)
$^1$H-NMR(DMSO-d$_6$) δ: 8.89(2H, brs), 8.57(1H, d, J=8 Hz), 8.44(1H, d, J=7.5 Hz), 7.80–7.60(2H, m), 7.14(1H, d, J=9.5 Hz), 4.12(2H, brs), 3.70(2H, brs), 3.30(2H, m), 3.09 (2H, m).

IR(KBr)cm$^{-1}$: 3380, 3280, 3130, 3010, 2804, 1703, 1643, 1611, 1472, 1405, 1307, 1207.

Compound 56

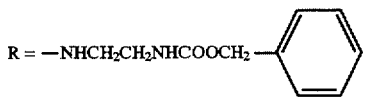

Ra=H

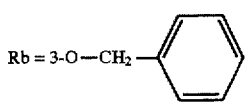

Yield: 45.1%
m.p.: 177°–178° C.
$^1$H-NMR(CDCl$_3$) δ: 8.15(1H, d, J=9 Hz), 7.99(1H, d, J=8 Hz), 7.67(1H, d, J=7 Hz), 7.54(1H, d-d, J=8,8 Hz), 7.45–7.23(11H, m), 7.15(1H, s), 7.03(1H, d-d, J=9,3 Hz), 6.54(1H, brs), 5.10(2H, s), 5.05(2H, s), 3.82(2H, m), 3.54 (2H, m).

IR(KBr)cm$^{-1}$: 3380, 1688, 1619, 1589, 1535, 1532, 1461, 1426, 1257, 1234, 1190, 1152.

Compound 57

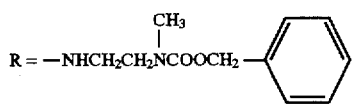

Ra=H

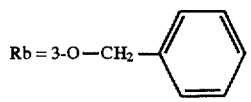

Yield: 67.8%
m.p.: 125°–128° C.
$^1$H-NMR(CDCl$_3$) δ: 8.14(1H, d, J=8 Hz), 7.98(1H, d, J=7 Hz), 7.66(1H, d, J=7 Hz), 7.56–7.13(13H, m), 7.03(1H, d-d, J=9,2 Hz), 5.17(2H, brs), 5.14(2H, s), 3.86(2H, m), 3.65(2H, brs), 3.04(3H, s).

IR(KBr)cm$^{-1}$: 2360, 1707, 1690, 1678, 1619, 1604, 1589, 1426, 1275, 1257, 1191, 1167.

Compound 58
R=—NHCH$_2$CH$_2$NHCH$_3$
Ra=H

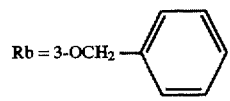

Yield: 26.3%
m.p.: 159°–162° C.

$^1$H-NMR(CDCl$_3$) δ: 7.90(1H, d, J=9 Hz), 7.72(1H, d, J=8 Hz), 7.54–7.25(7H, m), 7.16(1H, d-d, J=7,7 Hz), 6.99–6.93 (2H, m), 5.22(2H, s), 3.94(2H, brs), 3.37(2H, m), 2.81(3H, s).

IR(KBr)cm$^{-1}$: 3370, 1690, 1619, 1615, 1601, 1587, 1427, 1384, 1192.

Compound 59
R=—NHCH$_2$CH$_2$NH$_2$.2HCl.H$_2$O
Ra=H
Rb=3-OH
Yield: 63.7%
m.p.: 244° C. (decomp.)
$^1$H-NMR(DMSO-d$_6$) δ: 8.57(1H, d, J=9 Hz), 8.45(1H, d, J=8 Hz), 8.21(2H, brs), 7.85–7.63(4H, m), 7.17(1H, d, J=9 Hz), 4.11(2H, brs), 3.16(2H, m).

IR(KBr)cm$^{-1}$: 3000, 1699, 1643, 1623, 1615, 1479, 1315.

Compound 60
R=—NHCH$_2$CH$_2$NHCH$_3$.3HCl3/4H$_2$O
Ra=H
Rb=3-OH
Yield: 68.8%
m.p.: 202° C. (decomp.)
$^1$H-NMR(DMSO-d$_6$) δ: 8.79(2H, brs), 8.45(1H, d, J=9 Hz), 8.43(1H, d, J=7 Hz), 7.74–7.61(4H, m), 7.12(1H, d, J=9 Hz), 4.06(2H, brs), 3.25(2H, m), 2.63(3H, t, J=5 Hz).

IR(KBr)cm$^{-1}$: 3390, 1707, 1643, 1619, 1613, 1433, 1324, 1315, 1208.

Compound 61

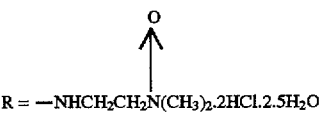

Ra=H
Rb=3-OH
Yield: 84.1%
m.p.: 212° C. (decomp.)
$^1$H-NMR(DMSO-d$_6$) δ: 8.56(1H, d, J=9 Hz), 8.43(1H, d, J=7.5 Hz), 7.80–7.40(4H, m), 7.15(1H, d, J=7 Hz), 4.40(2H, brs), 4.20–4.00(2H, m), 3.59(6H, s).

IR(KBr)cm$^{-1}$: 3410, 3370, 3300, 2830, 1702, 1655, 1624, 1614, 1479, 1315.

Compound 62
R=—OCH$_2$CH$_2$N(CH$_3$)$_2$
Ra=H
Rb=3-OH
Yield: 99.3%
m.p.: 182°–184° C.
$^1$H-NMR(CDCl$_3$) δ: 7.63(1H, d, J=7 Hz), 7.45(1H, d, J=9 Hz), 7.40–7.23(3H, m), 6.79(1H, brs), 6.74(1H, d, J=2 Hz), 6.69(1H, d-d, J=9,2 Hz), 4.60(2H, t, J=5 Hz), 3.02(2H, t, J=5 Hz), 2.64(6H, s).

IR(KBr)cm$^{-1}$: 1701, 1600, 1574, 1463, 1390, 1332, 1326, 1251, 1187, 1149.

Compound 63

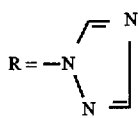

Ra=H

Rb = 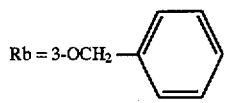

Yield: 50.6%
m.p.: 243°–247° C.
$^1$H-NMR(CDCl$_3$) δ: 9.14(1H, s), 8.49(1H, d, J=9 Hz), 8.24(1H, s), 8.17(1H, d, J=7.5 Hz), 7.80(1H, d-d, J=7.5,1 Hz), 7.70–7.35(9H, m), 5.25(2H, s).

IR(KBr)cm$^{-1}$: 3100, 1711, 1616, 1567, 1510, 1504, 1465, 1438, 1420, 1189, 1150, 1133, 989.

TABLE 2

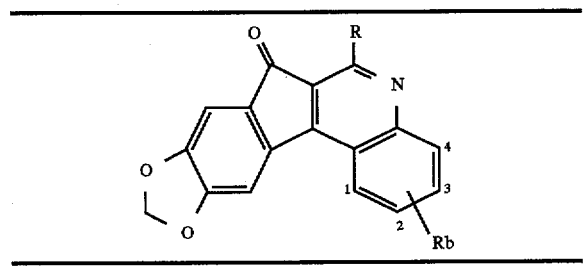

Compound 64
R=—OCH$_2$CH$_2$N(CH$_3$)$_2$
Rb=H
Yield: 68.1%
m.p.: 166°–167° C.
$^1$H-NMR(CDCl$_3$) δ: 8.21(1H, d, J=9 Hz), 7.83(1H, d-d, J=8,1 Hz), 7.69(1H, d-d-d, J=8,8,1 Hz), 7.50(1H, s), 7.44(1H, d-d-d, J=8,8,1 Hz), 7.13(1H, s), 6.11(2H, s), 4.72(2H, t, J=6 Hz), 2.87(2H, t, J=6 Hz), 2.42(6H, s).

IR(KBr)cm$^{-1}$: 3470, 2960, 2815, 2760, 1705, 1573, 1566, 1480, 1385, 1338, 1287, 1272, 1241, 1031.

Compound 64-a
R=—OCH$_2$CH$_2$N(CH$_3$)$_2$.HCl.3/2H$_2$O
Rb=H
m.p.: 215°–217° C.
IR(KBr)cm$^{-1}$: 3430, 2690, 1710, 1572, 1514, 1483, 1459, 1432, 1389, 1321, 1290, 1268, 1238, 1033.

Compound 65
R=—N(CH$_3$)CH$_2$CH$_2$N(CH$_3$)$_2$
Rb=H
Yield: 17.9%
m.p.: 102°–106° C.
$^1$H-NMR(CDCl$_3$) δ: 8.17(1H, d, J=8 Hz), 7.69(1H, m), 7.60(1H, m), 7.54(1H, s), 7.28(1H, m), 7.12(1H, s), 6.10(2H, s), 3.82(2H, t, J=7 Hz), 3.23(3H, s), 2.74(2H, t, J=7 Hz), 2.35(6H, s).

IR(KBr)cm$^{-1}$: 3460, 2945, 2760, 1695, 1566, 1543, 1514, 1501, 1479, 1417, 1372, 1292, 1036.

Compound 66
R=—NHCH$_2$CH$_2$N(CH$_3$)$_2$
Rb=H
Yield: 47.1%
m.p.: 208°–211° C.
$^1$H-NMR(CDCl$_3$) δ: 8.08(1H, d, J=9 Hz), 7.68(1H, d, J=8 Hz), 7.59(1H, m), 7.51(1H, s), 7.24(1H, m), 7.16(1H, brt), 7.12(1H, s), 6.11(2H, s), 3.75(2H, d-t, J=5,6 Hz), 2.62(2H, t, J=6 Hz), 2.34(6H, s).

IR(KBr)cm$^{-1}$: 3430, 3410, 3290, 1712, 1648, 1615, 1375, 1290, 1276, 1033.

Compound 66-a
R=—NHCH$_2$CH$_2$N(CH$_3$)$_2$.2HCl.3/4H$_2$O
Rb=H
m.p.: 237° C. (decomp.)
IR(KBr)cm$^{-1}$: 3290, 2690, 2661, 1713, 1648, 1615, 1504, 1473, 1453, 1394, 1376, 1347, 1289, 1276, 1031.

Compound 67
R=—NHCH$_2$CH$_2$N(CH$_3$)$_2$
Rb=3-OCH$_3$
Yield: 52.1%
m.p.: 205°–208° C.
$^1$H-NMR(CDCl$_3$) δ: 7.92(1H, d, J=9 Hz), 7.40(1H, s), 7.17(1H, brt), 7.08(1H, s), 7.02(1H, d, J=3 Hz), 6.87(1H, d-d, J=9,3 Hz), 6.09(2H, s), 3.94(3H, s), 3.73(2H, m), 2.61(2H, t, J=6 Hz), 2.34(6H, s).

IR(KBr)cm$^{-1}$: 3450, 3380, 1697, 1621, 1595, 1573, 1536, 1471, 1425, 1283, 1274, 1234, 1033.

Compound 68

R = 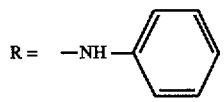

Rb=H
Yield: 40.4%
m.p.: 232°–235° C.
$^1$H-NMR(CDCl$_3$) δ: 8.99(1H, s), 8.06(1H, d, J=3 Hz), 7.96(2H, d, J=8 Hz), 7.80(1H, d, J=8 Hz), 7.63(1H, d-d, J=8,7 Hz), 7.45(1H, s), 7.38(2H, d-d, J=8,8 Hz), 7.30(1H, d-d, J=8,7 Hz), 7.10(1H, s), 7.06(1H, d-d, J=8,8 Hz), 6.10(2H, s).

IR(KBr)cm$^{-1}$: 1685, 1621, 1578, 1538, 1496, 1469, 1420, 1380, 1304, 1251, 1035, 747.

Compound 69
R=—NHCH$_2$CH$_2$N(C$_2$H$_5$)$_2$
Rb=H
Yield: 25.2%
m.p.: 128°–132° C.
$^1$H-NMR(CDCl$_3$) δ: 8.03(1H, d, J=8 Hz), 7.66(1H, d, J=8 Hz), 7.57(1H, d-d-d, J=8,8,1 Hz), 7.44(1H, s), 7.24–7.18(2H, m), 7.08(1H, s), 6.09(2H, s), 3.70(2H, d-t, J=6,6 Hz), 2.75(2H, t, J=6 Hz), 2.64(4H, q, J=7 Hz), 1.11(6H, s, J=7 Hz).

IR(KBr)cm$^{-1}$: 3480, 2980, 2790, 1703, 1591, 1376, 1283, 1032.

Compound 70

R = 

Rb=H
Yield: 51.2%
m.p.: 149°–153° C.
$^1$H-NMR(CDCl$_3$) δ: 8.05(1H, d, J=9 Hz), 7.67(1H, d, J=9 Hz), 7.58(1H, d-d-d, J=9,7,1 Hz), 7.48(1H, s), 7.23(1H, m), 7.13(1H, brs), 7.10(1H, s), 6.10(2H, s), 3.81(2H, d-t, J=7,6 Hz), 2.83(2H, t, J=7 Hz), 2.66(4H, brs), 1.84(4H, brs).

IR(KBr)cm$^{-1}$: 3480, 2900, 2800, 1690, 1593, 1530, 1477, 1375, 1032, 749.

Compound 71
R=—NHCH$_2$CH$_2$N(CH$_3$)CH$_2$CH$_2$N(CH$_3$)$_2$
Rb=H
Yield: 18.3%
m.p.: 116°–120° C.
$^1$H-NMR(CDCl$_3$) δ: 8.06(1H, d, J=8 Hz), 7.65(1H, d-d, J=9,1 Hz), 7.60–7.55(1H, m), 7.45(1H, s), 7.26–7.19(1H, m), 7.08(1H, s), 6.10(2H, s), 3.75(2H, m), 2.75–2.57(6H, m), 2.37(3H, s), 2.33(6H, s).
IR(KBr)cm$^{-1}$: 3470, 2950, 2820, 2770, 1699, 1596, 1563, 1532, 1497, 1475, 1374, 1292, 1279, 1245, 1030.

Compound 72
R=—NHCH$_2$CH$_2$N(CH$_3$)$_2$.2HCl
Rb=3-OH
Yield: 61.9%
m.p.: 225°–229° C.
$^1$H-NMR(D$_2$O) δ: 7.59(1H, d, J=9 Hz), 6.91–6.82(3H, m), 6.67(1H, s), 6.10(2H, s), 3.89(2H, t, J=6 Hz), 3.51(2H, t, J=6 Hz), 3.07(6H, s).
IR(KBr)cm$^{-1}$: 3400, 3030, 1699, 1642, 1622, 1446, 1367, 1285, 1270.

TABLE 3

[Chemical structure]

Compound 73
R=—NHCH$_2$CH$_2$N(CH$_3$)$_2$
Yield: 30.6%
m.p.: 182°–185° C.
$^1$H-NMR(CDCl$_3$) δ: 7.87(1H, d, J=8 Hz), 7.65(1H, d, J=7 Hz), 7.50(1H, d-d, J=8,8 Hz), 7.46(1H, s), 7.39(1H, d-d, J=8,7 Hz), 7.19(1H, brs), 7.04(1H, s), 6.08(2H, s), 3.74(2H, d-t, J=6,6 Hz), 2.62(2H, t, J=6 Hz), 2.34(6H, s).
IR(KBr)cm$^{-1}$: 3360, 2760, 1676, 1617, 1604, 1583, 1560, 1494, 1473, 1458, 1445, 1315, 1266, 1236, 1216, 1184, 1033.

Compound 73-a
R=—NHCH$_2$CH$_2$N(CH$_3$)$_2$.2HCl.H$_2$O
m.p.: 264° C. (decomp.)
IR(KBr)cm$^{-1}$: 3320, 3040, 2900, 1707, 1653, 1567, 1497, 1466, 1442, 1388, 1371, 1342, 1275, 1244, 1200, 1038.

TABLE 4

[Chemical structure]

Compound 74
R=—NHCH$_2$CH$_2$N(CH$_3$)$_2$
Yield: 58.4%
m.p.: 194°–196° C.
$^1$H-NMR(CDCl$_3$) δ: 8.97(1H, d, J=8 Hz), 8.29(1H, d, J=8 Hz), 8.17(1H, d, J=8 Hz), 8.01(1H, d, J=8 Hz), 7.79(1H, d, J=8 Hz), 7.70(1H, d, J=9 Hz), 7.63–7.54(2H, m), 7.46(1H, m), 7.31–7.27(2H, m), 3.79(2H, m), 2.66(2H, t, J=6 Hz), 2.37(6H, s).
IR(KBr)cm$^{-1}$: 3430, 3380, 1689, 1618, 1596, 1573, 1558, 1526, 812, 744.

TABLE 5

[Chemical structure]

Compound 75

R = —N⟨ ⟩N—CH$_3$

Ra=H
Rb=H
Yield: 32.3%
m.p.: 198°–201° C.
$^1$H-NMR(CDCl$_3$) δ: 8.37(1H, d, J=8 Hz), 8.16(1H, d, J=9 Hz), 7.83–7.62(4H, m), 7.48(1H, d-d, J=8,8 Hz), 7.27–7.22 (1H, m), 3.59(4H, t, J=5 Hz), 2.70(4H, t, J=5 Hz), 2.41(3H, s).
IR(KBr)cm$^{-1}$: 2790, 1715, 1461, 1420, 1405, 1363, 1285, 1261, 1141, 1008, 776, 724.

Compound 76
R=—N(CH$_3$)CH$_2$CH$_2$N(CH$_3$)$_2$.2HCl
Ra=H
Rb=H
Yield: 33.7%
m.p.: 210°–212° C.
$^1$H-NMR(DMSO-d$_6$) δ: 10.56(1H, brs), 8.59(1H, d, J=8 Hz), 8.40(1H, d, J=9 Hz), 8.12(1H, d, J=8 Hz), 7.95(1H, d-d, J=8,7 Hz), 7.81(1H, d-d, J=8,7 Hz), 7.64–7.56(1H, m), 7.34(1H, d-d, J=8,7 Hz), 3.88(2H, m), 3.46(2H, m), 3.23 (3H, s), 2.88(6H, d, J=5 Hz).
IR(KBr)cm$^{-1}$: 3360, 1712, 1521, 1454, 1405, 778, 721.

Compound 77
R=—N(CH$_3$)CH$_2$CH$_2$N(CH$_3$)$_2$.2HCl
Ra=9-OCH$_3$
Rb=H
Yield: 54.5%
m.p.: 115° C.
$^1$H-NMR(DMSO-d$_6$) δ: 10.50(1H, brs), 8.53(1H, d, J=8 Hz), 8.38(1H, d, J=8 Hz), 8.02(1H, d, J=8 Hz), 7.96–7.78 (2H, m), 7.14(1H, d, J=2.5 Hz), 7.08(1H, d-d, J=8,2.5 Hz), 3.86–3.81(5H, m), 3.44(2H, m), 3.18(3H, s), 2.86(6H, s).
IR(KBr)cm–1: 3410, 1714, 1479, 1467, 1457, 1432, 1403, 1390, 1290, 1224.

Compound 78
R=—OCH$_2$CH$_2$N(CH$_3$)$_2$
Ra=9-OCH$_3$
Rb=H
Yield: 38.5%
m.p.: 136°–137° C.
$^1$H-NMR(CDCl$_3$) δ: 8.39(1H, d, J=8 Hz), 8.27(1H, d, J=8 Hz), 7.81(1H, d-d-d, J=8,8,1 Hz ), 7.70–7.65(2H, m), 7.25 (1H, d, J=2.5 Hz), 6.93(1H, d-d, J=8,2.5 Hz), 4.75(2H, t, J=5.5 Hz), 3.87(3H, s), 2.88(2H, t, J=5.5 Hz), 2.40(6H, s).

IR(KBr)cm$^{-1}$: 2770, 1714, 1462, 1442, 1410, 1405, 1288, 1273, 1255, 786.

Compound 79

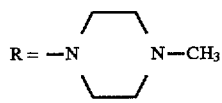

Ra=9-OCH$_3$
Rb=H
Yield: 41.1%
m.p.: 208°–210° C.
$^1$H-NMR(CDCl$_3$) δ: 8.31(1H, d, J=8 Hz), 8.16(1H, d, J=8.5 Hz), 7.79–7.61(3H, m), 7.27(1H, s), 6.94(1H, d-d, J=8,2.5 Hz), 3.87(3H, s), 3.55(4H, t, J=5 Hz), 2.70(4H, t, J=5 Hz), 2.41(3H, s).
IR(KBr)cm$^{-1}$: 2840, 1721, 1453, 1442, 1405, 1365, 1293, 1264, 1227, 798.

Compound 80
R=—OCH$_2$CH$_2$N(CH$_3$)$_2$
Ra=H
Rb=2-OCH$_3$
Yield: 43.6%
m.p.: 128°–132° C.
$^1$H-NMR(CDCl$_3$) δ: 8.32(1H, d, J=9 Hz), 7.73(1H, d, J=7 Hz), 7.65(1H, d, J=7 Hz), 7.57(1H, d, J=2 Hz), 7.48(1H, d-d, J=8,8 Hz), 7.31–7.22(2H, m), 4.74(2H, t, J=5 Hz), 4.04(3H, s), 2.86(2H, t, J=5 Hz), 2.40(6H, s).
IR(KBr)cm$^{-1}$: 2780, 1721, 1620, 1565, 1461, 1426, 1416, 1272, 1227, 1131.

Pharmacological Test Example 1 Cytotoxicity

P388 mouse leukemia cells were plated into 96-well plate at the density of 2×10$^3$ cells/well. The compounds of the invention were dissolved in purified water or dimethylsulfoxide and the solution was diluted with medium to various concentrations and added to respective wells. After the plate was incubated for 3 days, the cultures were fixed with glutaraldehyde and the number of survived cells were determined by crystal violet staining method.

Cytotoxic action of each compound was demonstrated as a compound concentration at which the number of cells were reduced to 50% of the number of cells of control, i.e., IC$_{50}$. The results are shown in table 6.

TABLE 6

| Compound Number | IC$_{50}$ (µg/ml) |
|---|---|
| 1-a | 2.4 × 10$^{-2}$ |
| 2 | 4.8 × 10$^{-3}$ |
| 7 | 6.5 × 10$^{-4}$ |
| 9-a | 7.4 × 10$^{-3}$ |
| 23-a | 1.1 × 10$^{-4}$ |
| 26-a | 4.2 × 10$^{-4}$ |
| 28-a | 2.0 × 10$^{-3}$ |
| 31-a | 6.0 × 10$^{-3}$ |
| 41-a | 1.1 × 10$^{-2}$ |
| 47-a | 1.3 × 10$^{-3}$ |
| 49-a | 2.0 × 10$^{-3}$ |
| 50-a | 1.1 × 10$^{-3}$ |
| 55 | 9.5 × 10$^{-4}$ |
| 60 | 6.6 × 10$^{-4}$ |
| 62 | 3.0 × 10$^{-4}$ |
| 64-a | 8.7 × 10$^{-4}$ |
| 66-a | 1.2 × 10$^{-3}$ |
| 73-a | 1.3 × 10$^{-2}$ |
| 75 | 4.5 × 10$^{-1}$ |
| 76 | 1.6 × 10$^{-1}$ |

Pharmacological Test Example 2 Antineoplastic action

P388 mouse leukemia cells (1×10$^6$ cells/mouse) were injected intraperitoneally into CDF$_1$ mouse. Each of the compound of the invention dissolved in 5% glucose or 5% dimethylsulfoxide at each of predetermined concentration was injected intraperitoneally on 1 and 5 days after injection. The antitumor activity thereof was evaluated as percentage of increase in life span (ILS %) compared to the mean survival of the untreated control group. The results are shown in table 7.

TABLE 7

| Compound No. | dose (mg/kg/day) | Increase in life span (ILS %) |
|---|---|---|
| 1-a | 100 | 68.0 |
| 2 | 67 | 85.0 |
| 3-a | 10 | 94.4 |
| 7 | 44 | 223.3 |
| 9-a | 150 | 60.0 |
| 26-a | 30 | 70.6 |
| 28-a | 67 | 180.0 |
| 31-a | 30 | 48.5 |
| 41-a | 67 | 305.8 |
| 47-a | 44 | 130.4 |
| 49-a | 150 | 66.7 |
| 50-a | 20 | 45.2 |
| 64-a | 67 | 152.9 |
| 66-a | 44 | 141.2 |
| 73-a | 44 | 129.4 |
| 76 | 100 | 75.0 |

Dosage Form Example 1 Capsules

Capsules were prepared in the conventional manner according to the following formulation.

| | |
|---|---|
| Compound 3-a | 200 mg |
| Lactose | 30 mg |
| Corn starch | 50 mg |
| Crystalline cellulose | 10 mg |
| Magnesium stearate | 3 mg |
| Per one capsule | 293 mg |

Dosage Form Example 2 Tablets

Tablets were prepared in the conventional manner according to the following formulation.

| | |
|---|---|
| Compound 7 | 100 mg |
| Lactose | 47 mg |
| Corn starch | 50 mg |
| Crystalline cellulose | 50 mg |
| Hydroxypropylcellulose | 15 mg |
| Talc | 2 mg |
| Magnesium stearate | 2 mg |
| Ethylcellulose | 30 mg |
| Unsaturated fatty acid glyceride | 2 mg |
| Titanium dioxide | 2 mg |
| Per one tablet | 300 mg |

Dosage Form Example 3 Granules

Granules were prepared in the conventional manner according to the following formulation.

| | |
|---|---|
| Compound 28-a | 200 mg |
| Mannitol | 540 mg |
| Corn starch | 100 mg |
| Crystalline cellulose | 100 mg |

-continued

| | |
|---|---|
| Hydroxypropylcellulose | 50 mg |
| Talc | 10 mg |
| Per one wrapper | 1000 mg |

Dosage Form Example 4 Fine granules

Fine granules were prepared in the conventional manner according to the following formulation.

| | |
|---|---|
| Compound 64-a | 200 mg |
| Mannitol | 520 mg |
| Corn starch | 100 mg |
| Crystalline cellulose | 100 mg |
| Hydroxypropylcellulose | 70 mg |
| Talc | 10 mg |
| Per one wrapper | 1000 mg |

Dosage Form Example 5 Injection

An injection was prepared in the conventional manner according to the following formulation.

| | |
|---|---|
| Compound 41-a | 100 mg |
| Distilled water for injection | suitable amount |
| Per one ampoule | 2 ml |

Dosage Form Example 6 Suppositories

Suppositories were prepared in the conventional manner according to the following formulation.

| | |
|---|---|
| Compound 73-a | 200 mg |
| Witepsol S-55 (registeredtrademark; a mixture of mono-, di- and triglycerides of saturated fatty acids consisting of lauric acid to stearic acids; product of Dynamit Nobel Co., Ltd.) | 1300 mg |
| Per one suppository | 1500 mg |

We claim:

1. A condensed-indan derivative represented by formula (1) or a pharmaceutically acceptable salt thereof:

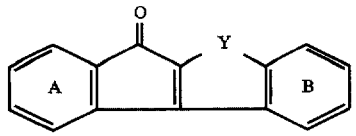

(1)

wherein ring A and ring B each independently represents (a) a benzene ring which is unsubstituted or has 1–4 substituents each independently selected from the group consisting of halogen atom, lower alkyl, lower alkoxy, hydroxyl, nitro, amino, lower alkylcarbonyloxy, benzyloxy, lower alkylcarbonylamino, cyano, carboxyl and lower alkoxycarbonyl, or (b) a benzene ring having a lower alkylenedioxy group, Y represents —N=CR— or —CR=N— wherein R represents (a) a —NR$_1$R$_2$ group, or (b) a —OR$_3$ group, wherein R$_1$ and R$_2$ are the same or different and each is independently selected from the group consisting of a hydrogen atom; a phenyl group; a 5- or 6-membered nitrogen-containing monocyclic heterocyclic group having 1–4 nitrogen atoms and 0–1 oxygen or sulfur atoms, and which is unsubstituted or has a lower alkyl group which is unsubstituted or substituted with at least one hydroxyl; and a lower alkyl group which is unsubstituted or substituted by at least one substituent selected from the group consisting of (a) an amino group which is unsubstituted or has 1–2 substituents selected from the group consisting of lower alkyl, lower cycloalkyl, di-loweralkylamino-alkyl, hydroxyloweralkyl, benzyloxycarbonyl, and lower alkanoyl, (b) lower alkoxy, (c) phenyl, (d) a 5- or 6-membered nitrogen-containing monocyclic heterocyclic group having 1–4 nitrogen atoms and 0–1 oxygen or sulfur atoms, (e) amine oxide substituted by a lower alkyl group and (f) at least one hydroxyl group; and R$_3$ represents a lower alkyl group which is unsubstituted or substituted by a substituted amino group which has 1–2 substituents selected from the group consisting of lower alkyl, lower cycloalkyl, di-loweralkylamino-alkyl, hydroxyloweralkyl, benzyloxycarbonyl, and lower alkanoyl.

2. The condensed-indan derivative or a pharmaceutically acceptable salt thereof according to claim 1, wherein the 1–4 substituents of benzene rings represented by ring A and ring B are each independently selected from the group consisting of halogen atom, lower alkyl, lower alkoxy, hydroxyl, nitro, amino, lower alkylcarbonyloxy, benzyloxy and lower alkylcarbonylamino.

3. The condensed-indan derivative or a pharmaceutically acceptable salt thereof according to claim 1, wherein R$_1$ and R$_2$ are the same or different and each is independently selected from the group consisting of a hydrogen atom; a phenyl group; and a lower alkyl group which is unsubstituted or substituted by at least one substituent selected from the group consisting of (a) an amino group which is unsubstituted or has 1–2 substituents selected from the group consisting of lower alkyl, lower cycloalkyl, di-loweralkylamino-alkyl, hydroxyloweralkyl, benzyloxycarbonyl and lower alkanol, (b) a 5- or 6-membered nitrogen-containing monocyclic heterocyclic group having 1–4 nitrogen atoms and 0–1 oxygen or sulfur atoms, (c) an amine oxide group substituted by lower alkyl group and (d) at least one hydroxyl group.

4. The condensed-indan derivative having indeno[2,1-c] quinoline skeleton or a pharmaceutically acceptable salt thereof according to claim 1, wherein Y represents —CR=N— wherein R represents (a) a —NR$_1$R$_2$ group wherein R$_1$ and R$_2$ are the same or different and each is independently selected from the group consisting of a hydrogen atom and a lower alkyl group which is unsubstituted or substituted by a diloweralkyl-substituted amino group or a 5- or 6-membered nitrogen-containing monocyclic heterocyclic group having 1–4 nitrogen atoms and 0–1 oxygen or sulfur atoms or (b) a —OR$_3$ group wherein R$_3$ represents a lower alkyl group which is unsubstituted or substituted by diloweralkyl-substituted amino group.

5. The condensed-indan derivative or a pharmaceutically acceptable salt thereof according to claim 4, wherein R$_1$ represents a lower alkyl group substituted by a diloweralkyl-substituted amino group or a 5- or 6-membered nitrogen-containing monocyclic heterocyclic group having 1–4 nitrogen atoms and 0–1 oxygen or sulfur atoms, and R$_2$ represents a hydrogen atom.

6. The condensed-indan derivative or a pharmaceutically acceptable salt thereof according to claim 4, wherein R$_1$ represents a lower alkyl group substituted by a substituent selected from the group consisting of dimethylamino, diethylamino and pyrrolidinyl.

7. The condensed-indan derivative or a pharmaceutically acceptable salt thereof according to claim 1, wherein ring B represents a benzene ring substituted by at least one hydroxyl group.

8. The condensed-indan derivative or a pharmaceutically acceptable salt thereof according to claim 1, wherein ring A represents a benzene ring which is unsubstituted or substituted by at least one hydroxyl group or at least one halogen atom.

9. The condensed-indan derivative or a pharmaceutically acceptable salt thereof according to claim 1, wherein ring A represents a benzene ring substituted by alkylenedioxy group.

10. The condensed-indan derivative having indeno[2,1-c] quinoline skeleton or a pharmaceutically acceptable salt thereof according to claim 1, wherein Y represents —CR=N—, R represents (a) a —NR$_1$R$_2$ group wherein R$_1$ and R$_2$ are the same or different and each is independently selected from the group consisting of a hydrogen atom and a lower alkyl group which is unsubstituted or substituted by a diloweralkyl-substituted amino group or a 5- or 6-membered nitrogen-containing monocyclic heterocyclic group having 1-4 nitrogen atoms and 0-1 oxygen or sulfur atoms, or (b) a —OR$_3$ group wherein R$_3$ represents a lower alkyl group which is unsubstituted or substituted by 25 diloweralkyl-substituted amino group, ring A represents (a) a benzene ring which is unsubstituted or substituted by 1 to 2 substituents each independently selected from the group consisting of hydroxyl and halogen, or (b) a benzene ring having a lower alkylenedioxy group, and ring B represents a benzene ring substituted by 1 to 2 hydroxyl.

11. The condensed-indan derivative having indeno[2,1-c] quinoline skeleton or a pharmaceutically acceptable salt thereof according to claim 1, wherein Y represents —CR=N— wherein R represents a —NR$_1$R$_2$ group wherein R$_1$ represents a lower alkyl group substituted by a diloweralkyl-substituted amino group or a 5- or 6-membered nitrogen-containing monocyclic heterocyclic group having 1-4 nitrogen atoms and 0-1 oxygen or sulfur atoms, and R$_2$ represents a hydrogen atom, ring A represents (a) a benzene ring which is unsubstituted or substituted by 1 to 2 substituents each independently selected from the group consisting of hydroxyl and halogen, or (b) a benzene ring having a lower alkylenedioxy group, and ring B represents a benzene ring substituted by 1 to 2 hydroxyl groups.

12. The condensed-indan derivative having indeno[2,1-c] quinoline skeleton or a pharmaceutically acceptable salt thereof according to claim 1, wherein Y represents —CR=N— wherein R represents a —NR$_1$R$_2$ group wherein R$_1$ represents a lower alkyl group having a substituent selected from the group consisting of dimethylamino, diethylamino and pyrrolidinyl and R$_2$ represents a hydrogen atom, ring A represents (a) a benzene ring which is unsubstituted or substituted by 1 to 2 substituents each independently selected from the group consisting of hydroxyl and halogen, or (b) a benzene ring having a lower alkylenedioxy group, and ring B represents a benzene ring substituted by 1 to 2 hydroxyl groups.

13. A composition comprising an effective amount of the condensed-indan derivative or a pharmaceutically acceptable salt thereof according to claim 1 and a pharmaceutically acceptable carrier therefor.

14. An antitumor agent suitable for treating a cancer tumor in a patient in need of such treatment, comprising a tumor-treating effective amount of a condensed-indan derivative or a pharmaceutically acceptable salt thereof and a pharmaceutically acceptable carrier therefor, said condensed-indan derivative being represented by formula (1)

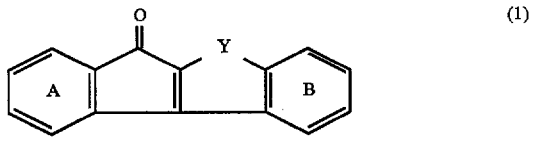

wherein ring A and ring B each independently represents
(a) a benzene ring which is unsubstituted or has 1-4 substituents each independently selected from the group consisting of halogen atom, lower alkyl, lower alkoxy, hydroxyl, nitro, amino, lower alkylcarbonyloxy, benzyloxy, lower alkylcarbonylamino, cyano, carboxyl and lower alkoxycarbonyl, or (b) a benzene ring having a lower alkylenedioxy group, Y represents —N=CR— or —CR=N— wherein R represents (a) a —NR$_1$R$_2$ group, (b) a 5- or 6-membered nitrogen-containing monocyclic heterocyclic group having 1-4 nitrogen atoms and 0-1 oxygen or sulfur atoms, and which is unsubstituted or has a lower alkyl group which is unsubstituted or substituted with at least one hydroxyl, or (c) a —OR$_3$ group, wherein R$_1$ and R$_2$ are the same or different and each is independently selected from the group consisting of a hydrogen atom; a phenyl group; a 5- or 6-membered nitrogen-containing monocyclic heterocyclic group having 1-4 nitrogen atoms and 0-1 oxygen or sulfur atoms, and which is unsubstituted or has a lower alkyl group which is unsubstituted or substituted with at least one hydroxyl; and a lower alkyl group which is unsubstituted or substituted by at least one substituent selected from the group consisting of (a) an amino group which is unsubstituted or has 1-2 substituents selected from the group consisting of lower alkyl, lower cycloalkyl, di-loweralkylamino-alkyl, hydroxyloweralkyl, benzyloxycarbonyl, and lower alkanoyl, (b) lower alkoxy, (c) phenyl, (d) a 5- or 6-membered nitrogen-containing monocyclic heterocyclic group having 1-4 nitrogen atoms and 0-1 oxygen or sulfur atoms, (e) amine oxide substituted by a lower alkyl group and (f) at least one hydroxyl group; and R$_3$ represents a lower alkyl group which is unsubstituted or substituted by a substituted amino group which has 1-2 substituents selected from the group consisting of lower alkyl, lower cycloalkyl, di-loweralkylamino-alkyl, hydroxyloweralkyl, benzyloxycarbonyl, and lower alkanoyl, with the proviso that when R represents a nitrogen-containing monocyclic heterocyclic group, at least one of ring A and ring B are other than a benzene ring without a substituent group.

15. The antitumor agent according to claim 14, wherein Y represents —N=CR— or —CR=N— wherein R represents (a) a —NR$_1$R$_2$ group or (b) a —OR$_3$ group, wherein R$_1$, R$_2$ and R$_3$ are as defined above.

16. A method for preparing a condensed-indan derivative represented by formula (1) comprising reacting a compound of formula (2) with a compound represented by RH:

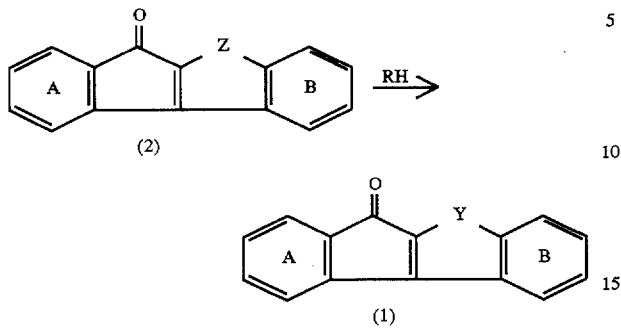

wherein ring A and ring B each independently represents (a) a benzene ring which is unsubstituted or has 1–4 substituents each independently selected from the group consisting halogen atom, lower alkyl, lower alkoxy, hydroxyl, nitro, amino, lower alkylcarbonyloxy, benzyloxy, lower alkylcarbonylamino, cyano, carboxyl and lower alkoxycarbonyl, or (b) a benzene ring having a lower alkylenedioxy group, Y represents —N=CR— or —CR=N— wherein R represents (a) a $NR_1R_2$ group or (b) a —$OR_3$ group, wherein $R_1$ and $R_2$ are the same or different and each is independently selected from the group consisting of a hydrogen atom; a phenyl group; a 5- or 6-membered nitrogen-containing monocyclic heterocyclic group having 1–4 nitrogen atoms and 0–1 oxygen or sulfur atoms, and which is unsubstituted or has a lower alkyl group which is unsubstituted or substituted with at least one hydroxyl; and a lower alkyl group which is unsubstituted or substituted by at least one substituent selected from the group consisting of (a) an amino group which is unsubstituted or has 1–2 substituents selected from the group consisting of lower alkyl, lower cycloalkyl, di-loweralkylamino-alkyl, hydroxyloweralkyl, benzyloxycarbonyl, and lower alkanoyl, (b) lower alkoxy, (c) phenyl, (d) a 5- or 6-membered nitrogen-containing monocyclic heterocyclic group having 1–4 nitrogen atoms and 0–1 oxygen or sulfur atoms, (e) amine oxide substituted by a lower alkyl group and (f) at least one hydroxyl group; and $R_3$ represents a lower alkyl group which is unsubstituted or substituted by a substituted amino group which has 1–2 substituents selected from the group consisting of lower alkyl, lower cycloalkyl, di-loweralkylamino-alkyl, hydroxyloweralkyl, benzyloxycarbonyl, and lower alkanoyl, Z represents —CX=N— or —N=CX— wherein X represents a halogen atom, and R in compound RH is as defined above.

* * * * *